(12) United States Patent
Chen et al.

(10) Patent No.: US 6,849,594 B1
(45) Date of Patent: Feb. 1, 2005

(54) PURIFICATION AND USE OF HUMAN RECOMBINANT CARTILAGE OLIGOMERIC MATRIX PROTEIN

(75) Inventors: Hui Chen, 50 Chester St. #50, Boston, MA (US) 02134; John W. Lawler, Swampscott, MA (US)

(73) Assignees: John Lawler, New York, NY (US); Hui Chen, New York, NY (US)

( * ) Notice: Subject to any disclaimer, the term of this patent is extended or adjusted under 35 U.S.C. 154(b) by 365 days.

(21) Appl. No.: 09/606,763

(22) Filed: Jun. 29, 2000

Related U.S. Application Data

(60) Provisional application No. 60/141,917, filed on Jun. 30, 1999.

(51) Int. Cl.[7] .................. A61K 38/00; C07K 14/00
(52) U.S. Cl. ............... 514/2; 530/350; 530/815; 536/23.1; 435/6; 435/69.1; 435/325; 435/320.1; 424/422; 424/520
(58) Field of Search .............. 514/2; 530/350, 530/815; 536/23.1; 435/6, 69.1, 325, 320.1; 424/422, 520

(56) References Cited

U.S. PATENT DOCUMENTS

| | | | |
|---|---|---|---|
| 4,666,702 A | * 5/1987 | Junginger et al. | 424/496 |
| 5,769,899 A | 6/1998 | Schwartz et al. | 623/18 |
| 5,842,477 A | 12/1998 | Naughton et al. | 128/898 |
| 5,872,094 A | 2/1999 | Goetinck et al. | 514/2 |

FOREIGN PATENT DOCUMENTS

| | | | |
|---|---|---|---|
| WO | WO 98/07035 | 2/1998 | |
| WO | WO 98/46253 | * 10/1998 | A61K/38/17 |

OTHER PUBLICATIONS

Hedbom et al., J. Biol. Chem 267, 6132–6136 (1992).*
Neidhart et al., British J. Rheumatology 36, 1151–1160 (1997).*
Newton, G., et al., "Characterization of Human and Mouse Cartilage Oligomeric Matrix Protein," *Genomics* 24 (3):435–439 (1994).
Oldberg, A., et al., "COMP (Cartilage Oligomeric Matrix Protein) Is Structurally Related to the Thrombospondins," *J. Biol. Chem.*, 267 (31):22346–22350 (1992).
Lawler, J., et al., "Cooperative Binding of Calcium to Thrombospondin," *J. Biol. Chem.*, 258:12098–12101 (1983).
DiCesare, P.E., et al., "Cartilage oligomeric matrix protein and thrombospondin 1; Purification from articular cartilage, electron microscopic structure, and chondrocyte binding," *Eur. J. Biochem.*, 223 (3):927–937 (1994).
Hecht, J.T., et al., "Characterization of Cartilage Oligomeric Matrix Protein (COMP) in Human Normal and Pseudoachondroplasia Musculoskeletal Tissues," *Matrix Biology*, 17:269–278 (1998).

* cited by examiner

*Primary Examiner*—Jon P. Weber
*Assistant Examiner*—Chih-Min Kam
(74) *Attorney, Agent, or Firm*—Hamilton, Brook, Smith & Reynolds, P.C.

(57) ABSTRACT

The invention relates to purified cartilage oligomeric matrix protein (COMP), such as human COMP (hCOMP), including hCOMP prepared by purifying hCOMP in the presence of calcium (e.g. under calcium replete conditions); methods of purifying COMP in the presence of calcium; antibodies to purified hCOMP; ELISA kits comprising purified hCOMP; compositions (e.g. implants) comprising COMP; methods of repairing or producing cartilage comprising implanting a composition comprising COMP and a differentiation agent; methods for making an implant for cartilage repair comprising binding a differentiation agent to hCOMP; methods of transplanting chondrocytes and mesenchymal stem cells comprising culturing the cells in the presence of hCOMP; methods of transplanting chondrocytes comprising culturing them in the presence of hCOMP; methods of mediating attachment of cells using differentiation agent-bound COMP; methods of preparing a cartilage repair composition comprising culturing and purifying COMP in the presence of calcium and adding it to a matrix; and assays and methods of detection and quantification of COMP (e.g. degraded COMP and non-degraded COMP) and anti-COMP antibodies in a sample.

8 Claims, 6 Drawing Sheets

SEQUENCE LISTING

<160> NUMBER OF SEQ ID NOS: 1

<210> SEQ ID NO 1
<211> LENGTH: 13
<212> TYPE: PRT
<213> ORGANISM: Unknown
<220> FEATURE:

-continued

```
<223> OTHER INFORMATION: calcium binding concensus sequence
<221> NAME/KEY: CA_BIND
<222> LOCATION: (1)...(13)
<221> NAME/KEY: VARIANT
<222> LOCATION: (1)...(13)
<223> OTHER INFORMATION: Xaa = Any Amino Acid

<400> SEQUENCE: 1

Asp Xaa Asp Xaa Asp Gly Xaa Xaa Asp Xaa Xaa Asp Xaa
 1               5                  10
```

PURIFICATION AND USE OF HUMAN RECOMBINANT CARTILAGE OLIGOMERIC MATRIX PROTEIN

RELATED APPLICATION

This application claims the benefit of U.S. Provisional Application No. 60/141,917, filed Jun. 30, 1999, the entire teachings of which are incorporated herein by reference.

GOVERNMENT SUPPORT

The invention was supported, in whole or in part, by grant HL 49081 from the Heart, Lung and Blood Institute from the National Institutes of Health. The Government has certain rights in the invention.

BACKGROUND OF THE INVENTION

Hyaline cartilage is a specialized connective tissue that plays an important role in dissipating loads in joints. It provides a smooth, low friction gliding surface that has resilience and resistance to compression and shear forces. It is composed of terminally differentiated chondrocytes embedded within an extracellular matrix that is produced, elaborated and maintained by the cells themselves. The extracellular matrix of cartilage is composed of three classes of molecules. The first is highly cross-linked fibrils of triple helical type II collagens that interact with other cartilage specific collagens, including type II and XI collagens. The abundant large aggregating proteoglycan aggrecan as well as some small proteoglycans such as biglycan and decorin comprise the second class. These proteoglycans contain chondroitin sulfates as their glycosaminoglycans side chains. The third class of proteins are non-collagenous proteins including cartilage oligomeric matrix protein (COMP; also sometimes referred to as thrombospondin-5) and link protein. The proper composition and arrangement of the cartilage extracellular matrix are important for maintaining the proper amount of water and electrolyte in the matrix, thus conferring its mechanical properties.

Seemingly inert and able to tolerate a tremendous amount of physical stress, cartilage can be damaged by a variety of mechanical, chemical and microbiological agents, often resulting in pain, swelling, loss of motion, and eventually disabling arthritis. The biggest limitation of cartilage is that it is incapable of healing. This inherent inability to repair is due to its avascularity, the immobility of chondrocytes, and the limited ability of mature chondrocytes to proliferate and alter their synthetic pattern. Various methods of stimulating cartilage repair have been used with varying success. Major surgical methods for treating osteoarthritis include tissue transplantation, chondrocyte and mesenchymal stem cell transplantation, and transplantation of artificial matrices including collagen gels, carbon fiber pads, and porous polylactic acids and other biodegradable synthetic matrices. Because of the limited availability of cartilage tissue for transplantation, therapeutic efforts have been focused on the transplantation of cells and matrices in creating a regenerated tissue resembling articular cartilage in its structure and its biochemical and mechanical properties. However, despite numerous efforts by numerous research labs and companies, the outcome of these methods is generally mixed and not very satisfactory. It would be useful to develop a better method of cartilage repair.

SUMMARY OF THE INVENTION

Recombinant human cartilage oligomeric matrix protein (COMP) in a mammalian system has been produced and purified. The purified hCOMP has several properties that make it much more advantageous than the purified COMP reported before. hCOMP is purified in a calcium replete conformation, which preserves the structure and function of the type 3 calcium binding repeats and therefore preserves the native structure and function of the protein. The hCOMP is a glycosaminoglycan (GAG) binding protein. It binds to GAGs including heparin and chondroitin sulfates. Chondroitin sulfate is the major component of the proteoglycans found in cartilage. Heparin binding also provides a very convenient way for hCOMP purification from the conditioned medium. This is in contrast to the previous report that COMP purified in the presence of EDTA can not bind to heparin. hCOMP is demonstrated to have a better affinity for GAGs in a calcium replete form. COMP is demonstrated to be without doubt an adhesive protein for chondrocytes, whether the chondrocytes are differentiated or de-differentiated. The data also show that COMP needs to be in its calcium-replete conformation for its maximal cell adhesive activity. COMP is also shown to serve as a motility factor to promote chondrocyte migration. These properties of COMP, along with its ability to bind collagen, and differentiation regulating reagents retinoic acid and vitamin $D_3$ and its metabolites, make COMP a very attractive agent for use in the research of cartilage repair. COMP can be used in chondrocyte transplantation and artificial matrix transplantation in cartilage repair in light of COMP's ability to serve as a chemoattractive and an adhesive substrate for the cells, and as a reagent for delivering retinoic acid and vitamin $D_3$ and its metabolites to promote and maintain chondrocyte differentiation and production of the correct cartilage matrix.

The invention includes purified COMP, such as human COMP (hCOMP), including hCOMP prepared by expressing and/or purifying hCOMP in the presence of calcium, and methods of purifying COMP (e.g., hCOMP) in the presence of calcium. The COMP can be purified in a calcium-replete environment, for example, where calcium is present at a millimolar range (level), e.g. at least 300 $\mu$M (0.3 millimolar). In one embodiment, hCOMP clones are introduced into cells, for example cells capable of expressing and secreting hCOMP; the cells are cultured, e.g. in a medium under conditions suitable for expressing the hCOMP; and the hCOMP is purified in the presence of calcium. The hCOMP clones can be produced by transfecting suitable cells with DNA encoding full length hCOMP ("hCOMP DNA") (Newton et al., 1994). The hCOMP can be purified under calcium-replete conditions, for example, millimolar levels (i.e. in the milimolar range). The cells can be cultured in a calcium-replete culture medium. The hCOMP can be expressed and/or purified in an environment (e.g., in a solution) characterized by a calcium concentration of at least 300 $\mu$M. Cells capable of expressing COMP include some fibroblasts, chondrocytes, tendon, ligament, smooth muscle cells, pericytes, and human embryonic kidney cells or other cells transfected with DNA encoding COMP, for example.

In one embodiment, hCOMP produced by the methods herein digests into bands of 50 kDa or 55 kDa when cleaved by trypsin. In another, purified hCOMP can be digested into bands of 62 kDa or 67 kDa when cleaved by trypsin.

Fragments, mutant forms and other derivatives and analogs of COrvP (e.g. human COMP, such as hCOMP purified by the methods described herein) are also encompassed withing the invention, as well as methods of making and using such fragments, mutants and other derivatives and analogs. In one embodiment, such derivatives include the binding sites (e.g. the calcium binding sites) of COMP, particularly COMP in its calcium-replete conformation. Also included are compositions which include COMP and/or a COMP derivative.

The invention also encompasses antibodies to hCOMP purified in the presence of calcium, for example, hCOMP purified under the methods disclosed herein. In one embodiment, the antibody is to purified hCOMP which is prepared by introducing hCOMP clones into cells capable of expressing and secreting hCOMP, culturing the cells in a culture medium under conditions suitable for expressing the hCOMP; and purifying the hCOMP in the presence of calcium. In another embodiment, the antibody is an antibody to the hCOMP purified in a calcium-replete environment, for example, where calcium is present at a millimolar range (level), e.g. at least 300 $\mu$M (or 0.3 millimolar). The anti-COMP antibodies can be monoclonal or polyclonal.

The invention also encompasses ELISA kits comprising purified hCOMP which is prepared by introducing hCOMP DNA into cells, thereby producing transfected cells capable of expressing and secreting hCOMP, culturing the cells in a culture medium under conditions suitable for expressing the hCOMP; and purifying the hCOMP in the presence of calcium. In one embodiment, the invention comprises antibodies to such hCOMP.

The invention also encompasses compositions (e.g. implants) comprising a matrix comprising COMP (e.g. hCOMP). The matrices of the invention can be biological or nonbiological. They can be artificial. They can comprise treated cartilage and bone matrices, collagens, hyaluronan, fibrin gels, carbon fibers, porous polylactic acid, type I collagen gel and type II collagen gel. In one embodiment, the matrix comprises type I or type II collagen gel. The matrix can be seeded (e.g. embedded) with cells, for example, chondrogenic cells, e.g. mesenchymal stem cells or chondrocytes. A differentiation agent (i.e., differentiation factor) can be bound to the hCOMP. The differentiation agent can be, for example, vitamin $D_3$ or at least one vitamin $D_3$ metabolite (e.g. 1,25-dihydroxyvitamin $D_3$ and 24R,25-dihydroxyvitamin $D_3$) or retinoic acid. The implant can comprise at least one proteoglycan, for example, a chondroitin sulfate proteoglycan. In one embodiment, the matrix comprises purified hCOMP produced by introducing hCOMP clones into cells, for example cells capable of expressing and secreting hCOMP; culturing the cells, e.g. in a medium under conditions suitable for expressing the hCOMP; and purifying the hCOMP in the presence of calcium. The COMP can be recombinant human COMP, for example, purified human COMP secreted by cells cultured in a calcium-replete environment and purified in the presence of calcium. The COMP can be hCOMP purified in a calcium-replete environment. The matrix can also include growth factors.

The invention also includes methods of repairing (or producing) cartilage, e.g. at a cartilage defect area, comprising implanting into the defect area a composition comprising COMP associated with (e.g. bound to) a differentiation agent. The defect area can be a site in need of cartilage repair. The differentiation agent can be vitamin $D_3$ or vitamin $D_3$ metabolites (e.g. 1,25-dihydroxyvitamin $D_3$ and 24R,25-dihydroxyvitamin $D_3$) or retinoic acid. One or more proteoglycans such as chondroitin sulfate proteoglycan can be added to the composition prior to implantation. The hCOMP can act as a bridge between the collagen and the proteoglycan. The composition can be a matrix. The COMP can be human COMP. The COMP can be secreted by cells cultured in a calcium-replete environment and purified in the presence of calcium. In one embodiment, the COBP is purified hCOMP produced by introducing hCOMP clones into cells, for example cells capable of expressing and secreting hCOMP; culturing the cells, e.g. in a medium under conditions suitable for expressing the hCOMP; and purifying the hCOMP in the presence of calcium. The COMP can recombinant.

The invention also includes methods for making an implant for cartilage repair comprising binding a differentiation agent to hCOMP, and adding the differentiation agent-bound hCOMP to a matrix. The hCOMP can mediate delivery of the differentiation agent (e.g. to the cells) and release of the differentiation agent, and serves as a chemoattractant (a migration factor) for chondrocytes. One embodiment further comprises adding (e.g. seeding) chondrogenic cells to the matrix. The hCOMP mediates delivery to the cells of the differentiation agent and release of the differentiation agent, helping to maintain and promote the chondrogenic cells to mature and differentiate, thereby producing naturally occuring non-traumatic cartilage matrix.

In another embodiment, the invention encompasses methods of transplanting cells (for example, chondrogenic cells, e.g. chondrocytes, such as autologous chondrocytes) comprising culturing the cells in the presence of hCOMP (which can be bound with a differentiation agent). The cells can be isolated from an animal, such as a mammal, e.g. a human (for example, a patient). The hCOMP can mediate attachment of the expanded chondrocytes and provide delivery and release of the differentiation agent. The cells can be cultured on tissue culture plates coated with hCOMP bound with a differentiation agent. The differentiation agent can be vitamin $D_3$ or vitamin $D_3$ metabolites or retinoic acid. Cells, e.g. chondrocytes and mesenchymal stem cells, can be injected in the presence of hCOMP with a bound differentiation agent into the defect area, thereby aiding in the maintenance of differentiated chondrocytes and stimulating production of type II collagen and other cartilage components by the chondrocytes in the defect areas. The cells can be cultured in the presence of hCOMP (which can be bound with a differentiation agent). The hCOMP can be purified by the methods described herein. The invention also encompasses producing chondrocytes for autologous transplantation using these methods, and the chondrocytes produced by these methods.

The invention also encompasses methods of mediating attachment of cells, e.g. chondrogenic cells (for example, chondrocytes and mesenchymal stem cells) in transplantation (non-autologous or autologous) comprising injecting the cells in the presence of differentiation agent-bound COMP into the defect area, thereby creating and aiding in the maintenance of the differentiation stage of cells and stimulating production of type II collagen and other cartilage components by the cells in the defect areas.

The invention also encompasses methods of preparing a composition (e.g. an implant) for cartilage repair comprising culturing and purifying COMP in the presence of calcium (e.g. a calcium-replete environment) and adding it to a matrix, for example, a matrix described herein. The matrix can be seeded with cells, e.g. chondrocytes or mesenchymal stem cells, prior to implantation. The COMP can be expressed from cells transfected with COMP and cultured in a calcium-replete environment, under conditions appropriate for processing and secretion of COMP. Chondrogenic cells can be proliferated in vitro in the presence of said COMP, and the chondrogenic cells can be added (e.g. seeded) into a matrix. These cells can be seeded into the matrix in the presence of COMP.

The invention also includes assays and methods of detection and quantification of COMP (e.g. degraded COMP and non-degraded COMP including fragments) and COMP antibodies, for example in a sample. The sample can be biological, e.g. fluid, for example, serum or synovial fluid. The COMP can be hCOMP, such as hCOMP produced or purified by the methods described herein. The anti-COMP antibodies can be the antibodies described herein. The sample can be serially diluted. The COMP can be detected with a labeled reagent, such as an enzyme conjugated secondary antibody. The level of bound COMP or bound anti-COMP antibody or degraded COMP (e.g., degraded fragments of COMP) in the assays can be measured by ELISA, e.g. competitive ELISA.

In one embodiment, a biological sample can be contacted with an anti-COMP antibody (such as one described herein) under conditions suitable for binding the anti-COMP antibody to hCOMP in the biological sample, thereby producing bound hCOMP. The bound hCOMP can be detected, and the amount of bound hCOMP in the sample can be compared to known amounts of bound hCOMP which form a standard curve, whereby the amount of hCOMP in the sample is measured. In another embodiment, the presence of hCOMP in a biological sample can be measured by incubating the biological sample with an anti-COMP antibody, under conditions suitable for binding the anti-COMP antibody to hCOMP in the biological sample. The biological sample can be added to a plate which has been coated with the purified hCOMP as described herein, and after washing, hCOMP bound to the plate in the biological sample can be detected. The amount of bound hCOMP in the sample can be compared to known amounts of hCOMP which form a standard curve, whereby the amount of hCOMP is measured. Yet another embodiment involves an assay to detect anti-COMP antibodies in a biological sample comprising coating purified hCOMP on a plate, serially diluting the sample, contacting the serial dilutions with the hCOMP, and detecting the presence of bound anti-hCOMP antibodies with a labeled reagent that specifically binds to hCOMP. The presence or progression of arthritis (such as rheumatoid arthritis or osteoarthritis) in a mammal (e.g. a human, for example a patient) can be detected by the methods described herein. Degraded COMP can be detected in a similar manner, using antibodies which recognize degraded fragments of COMP.

Also included in the invention are methods of detecting degradation of COMP comprising detecting COMP with an immunoblot assay, for example, an immunoblot assay using anti-COMP antibodies as described herein that recognize the degraded and forms (e.g., degraded fragments) of COMP. The anti-COMP antibodies can be polyclonal antibodies or monoclonal antibodies. The regular intensities of bands created by the immunoblot method can be scanned and the percentage of degraded bands can be calculated. The COMP can be hCOMP, for example hCOMP purified by the methods described herein. A molecular mass standard can be used for identifying the intact and degraded forms of COMP. These immunoblot assays can be used to detect inflammatory joint disease such as rheumatoid arthritis or osteoarthritis, by comparing the amount of degraded COMP measured with the amount of COMP in other mammals, for example, mammals which have such joint disease or mammals that do not have such joint disease.

DETAILED DESCRIPTION OF THE INVENTION

Cartilage oligomeric matrix protein (COMP) is a pentameric extracellular matrix protein. It is primarily localized in the chondrocyte territorial matrix, and can also be found in synovium, tendon and ligament (Hedbom et al., 1992; DiCesare et al., 1994; DiCesare et al., 1997; Hecht et al., 1998). COMP is the fifth member of the thrombospondin (TSP) family. Compared to the other TSPs, COMP is the only member that lacks the $NH_2$-terminal heparin binding domain, and it has been reported not to bind to heparin-agarose (DiCesare et al., 1994; Hauser et al., 1995). Similar to other TSPs, COMP has a coiled-coil region responsible for multimerization and interchain disulfide bonds, four EGF-like type 2 repeats, seven highly conserved type 3 repeats that consist of 13 calcium-binding loops, and a COOH-terminal globular domain (Oldberg et al., 1992; Newton et al., 1994). COMP mutations lead to human skeletal dysplasias, including pseudoachondroplasia and multiple epiphyseal dysplasia, Fairbanks type. These are autosomal dominant mutations that affect normal bone and cartilage formation. Most of the mutations are located in the type 3 repeats and some in the C-globe region (Briggs et al., 1995; Hecht et al., 1995).

The large number of consecutive calcium-binding consensus repeats is unique to TSPs. The aspartate-rich sequences are similar to sequences in calcium-binding sites of a class of calcium-binding proteins including calmodulin, parvalbumin and fibrinogen (Lawler and Hynes, 1986). Variations of the calcium-binding consensus sequence DXDXDGXXDXXDX (SEQ ID NO: 1) occur thirteen times in a TSP subunit and have been proposed to form calcium-binding loops (Lawler and Hynes, 1986; Sun et al., 1992; Misenheimer and Mosher, 1995). Equilibrium dialysis, circular dichroism and limited trypsin digestion studies on TSP1 suggest that each TSP1 subunit binds 11–12 calcium ions in a cooperative fashion. Most of the calcium-binding activity can be attributed to the type 3 repeats. These studies also suggest that there is a conformational change when TSP 1 binds calcium (Lawler and Simons, 1983; Misenheimer and Mosher, 1995). The type 3 repeats are highly conserved in all TSP molecules. According to the presence of the type 3 repeats in COMP and studies on TSP1, COMP is predicted to bind calcium and display different conformations in the presence and absence of calcium. However, COMP, originally purified in the presence of EDTA, did not bind calcium, and failed to show a significant conformational difference as a function of calcium (Rosenberg et al., 1998; Hauser et al., 1995; Morgelin et al., 1992; DiCesare et al., 1994).

Figure 1:
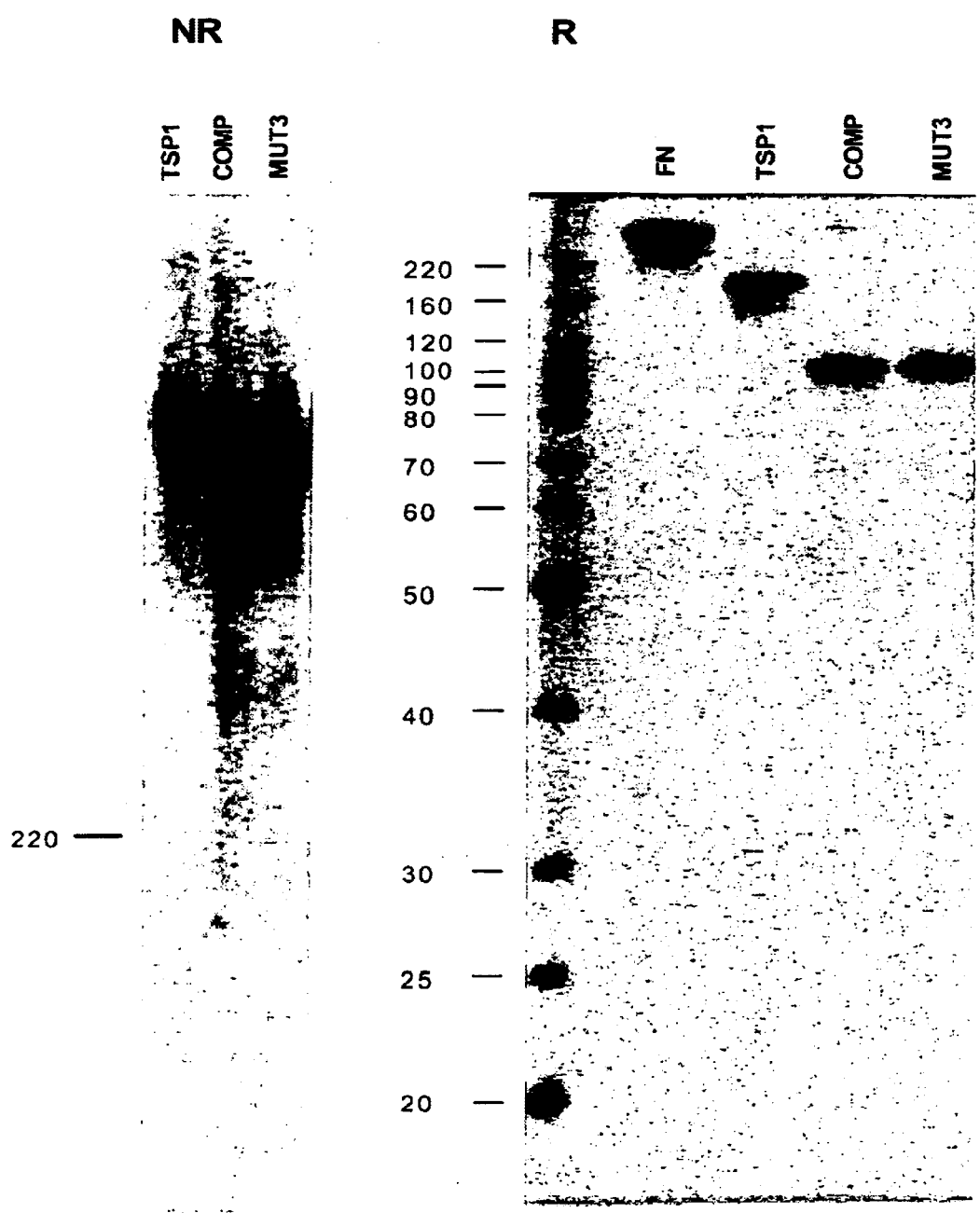
FIG. 1 depicts SDS-PAGE of purified recombinant COMP. Recombinant human COMP expressed by human embryonic kidney 293 cells were purified from conditioned medium. Purified hCOMP was analyzed by polyacrylamide gel electrophoresis in SDS under non-reducing (NR) or reducing (R) conditions. Size markers are as labeled. TSP1 stands for human thrombospondin 1. MUT3 is a mutant form of COMP.

As discussed in Example 1, full length human COMP sequence was cloned and the resulting full length sequence was cloned into a mammalian expression vector and were transfected into human embryonic kidney cells. Colonies of stable transfectants were isolated and expanded. When the human embryonic kidney cells were transfected with full length human COMP cDNA, they were able to process and secrete hCOMP (FIG. 1).

In addition, as demonstrated in Example 2, COMP is a calcium binding protein. According to the presence of the type 3 repeats in COMP and studies on TSP1, COMP is predicted to bind calcium. However, COMP, originally purified in the presence of EDTA, did not bind calcium, and failed to show a significant conformational difference as a function of calcium (Rosenberg et al., 1998; Hauser et al., 1995; Mörgelin et al., 1992; DiCesare et al., 1994). Here, direct calcium binding, rotary shadowing electron microscopy (EM) and limited trypsin digestion was used to show that COMP is a calcium binding protein and displays different conformation under different calcium concentrations.

Figure 2:
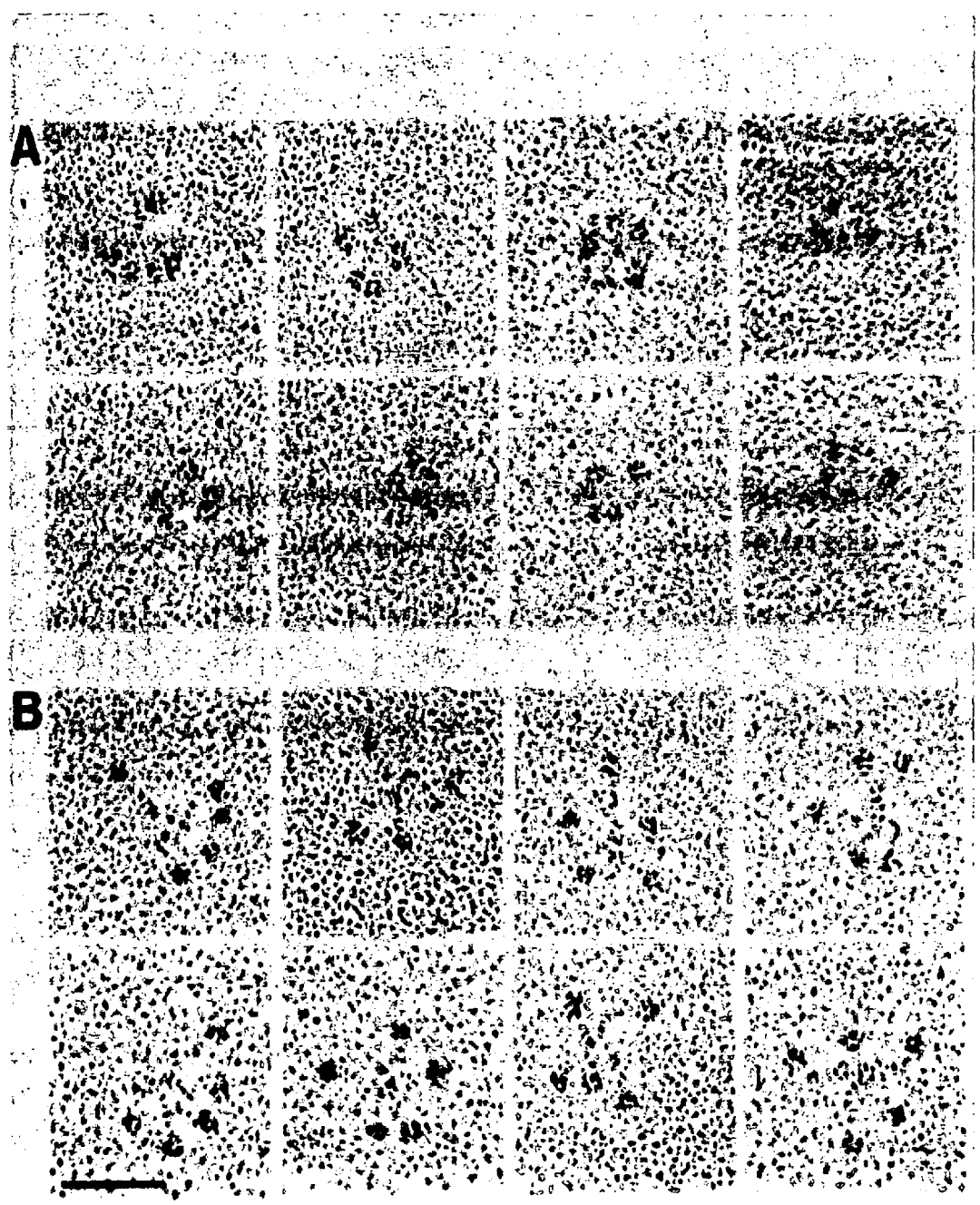
FIG. 2 depicts rotary shadowing electron microscopy images of human recombinant COMP. Purified COMP in Tris-buffered saline containing $CaCl_2$ (A). COMP adjusted to 5 mM EDTA before spraying (B). The bar equals 50 nm.

Rotary shadowing EM images (FIG. 2) of hCOMP show that recombinant hCOMP is a pentamer. In the presence of calcium, hCOMP had a compact appearance which made it difficult to resolve the five subunits. In the presence of EDTA, hCOMP adopted an extended conformation. These results suggested that hCOMP, when purified in a calcium replete form, will undergo conformational changes when calcium is chelated from the molecules. This observation differed from previously published reports on COMP purified in the presence of EDTA (Mörgelin et al., 1992; DiCesare et al., 1994). However, the conformational change observed herein was consistent with previous findings on TSP1, TSP3 and TSP4 and with the presence of the highly homologous type 3 calcium-binding repeats on COMP (Lawler et al., 1982; Qabar et al., 1995; Lawler et al., 1995; Oldberg et al., 1992; Newton et al., 1994).

Figure 3:
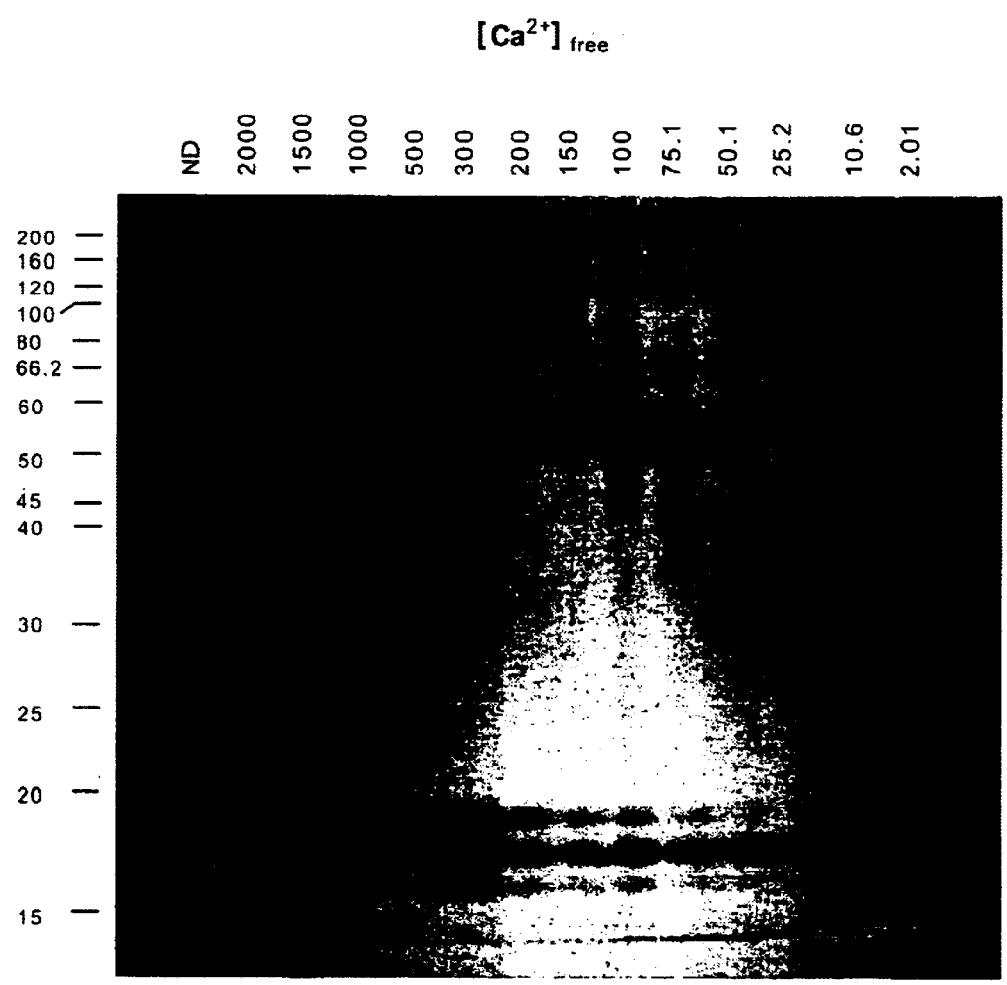
FIG. 3 depicts limited trypsin digestion of COMP at varying calcium concentrations. Molecular size markers are as indicated. ND: non-digested proteins.

To further show that hCOMP is a calcium binding protein, limited trypsin digestion of hCOMP was performed under various calcium concentrations. At low calcium concentrations, hCOMP was readily cleaved by trypsin into two small fragments at 27 kDa and 36 kDa (FIG. 3). When the calcium concentration increased, hCOMP was digested into intermediate bands at 50 kDa and 55 kDa. When calcium concentration was higher with increasing calcium concentrations, 62 kDa and 67 kDa bands of hCOMP started to appear. The 67 kDa band became the prevalent band at calcium concentrations in the millimolar range. These results demonstrated that hCOMP has different susceptibilities to trypsin digestion that are dependent on calcium concentrations, and suggested that conformational differences related to the type 3 calcium-binding repeats are present.

Direct calcium binding to COMP was measured by equilibrium dialysis using $^{45}CaCl_2$. Briefly, TSP1 and COMP were dialyzed in Slide-A-Lyzer dialysis units (Pierce, Rockford, Ill.) against dialysis buffer containing 0.3 mM $CaCl_2$ and 10 $\mu$Ci/Cml of $^{45}CaCl_2$. At the end of dialysis, 10 $\mu$l of protein sample and dialysis buffer were taken out for scintillation counting and protein determination. The number of calcium ions bound was calculated. At 0.3 mM free calcium concentration, each TSP1 subunit bound 10±2 calcium ions (mean±SD of four data points). This is in agreement with previous reports where 11–12 calcium ions were reported to bind to each TSP1 subunit (Lawler and Simons, 1983; Misenheimer and Mosher, 1995). Under the same conditions, each subunit of COMP bound 11±1 calcium ions. This is the first time it is shown that COMP binds calcium ions, and the result is consistent with the presence of highly homologous type 3 calcium binding repeats in COMP and other TSP family members.

Moreover, as demonstrated herein in Example 3, COMP is a glycosaminoglycan (GAG) binding protein, with maximal binding dependent on its calcium-replete conformation. To probe whether hCOMP could be a GAG-binding protein despite its lack of the $NH_2$-terminal heparin binding domain, and whether the conformation of the type 3 calcium-binding repeats could affect functions of hCOMP, the interaction of hCOMP with common GAGs found in cartilage was tested in the presence of either calcium or EDTA.

Affinity co-electrophoresis (ACE) was used to quantify the binding of hCOMP to heparin and other GAGs, including chondroitin sulfates from cartilage. The results of these analyses are presented in Table 1. Values are given in nM, and in cases where a standard deviation is reported, represent the mean of two determinations. Where data are reported as greater than a given value, it indicates that no binding was observed at any protein concentration.

TABLE 1

Binding of hCOMP to glycosaminoglycans.

| GAG | COMP, $K_d$ in 2 mM $Ca^{2+}$ | COMP, $K_d$ in 5 mM EDTA |
|---|---|---|
| Heparin porcine intestine, <6 kD | 89 (±22) | 450 |
| C4S bovine trachea | 583 (±75) | — |
| C6S shark cartilage | 403 (±110) | >11000 |
| DS porcine skin | 328 (±25) | — |
| HS bovine kidney | 1200 | — |
| KS bovine cornea | >11000 | — |

COMP bound low molecular weight heparin. This is in agreement with our observation that hCOMP binds to heparin-Sepharose. While binding to heparin may suggest the presence of functional GAG-binding sites in COMP, heparin is a highly sulfated form of HS that is made only in mast cells, and therefore is not truly representative of GAGs from most tissues. To better ascertain potential roles of GAGs and proteoglycans in COMP function, heparan sulfate, keratan sulfate, and three chondroitin sulfates (chondroitin-6-sulfate, C6S; chondroitin-4-sulfate; C4S; and
dermatan sulfate, DS) were tested for binding to hCOMP in the presence of calcium using ACE (Table 1). The data revealed that hCOMP bound to the three chondroitin sulfates with comparable affinities, while binding to HS was weaker (1.2 $\mu$M). hCOMP did not bind to keratan sulfate.

To further determine whether the conformation of the calcium-binding type 3 repeats was critical to GAG binding, hCOMP was tested for binding to heparin and C6S in the presence of EDTA. These results demonstrated that depletion of calcium reduced hCOMP binding to GAGs. While heparin binding was reduced only 3- to 5- fold by EDTA treatment, C6S binding appeared to be abolished by this treatment, thus suggesting the existence of a conformation-dependent CS-binding site in the type 3 repeats and/or C-terminus domains. This indicates that COMP needs to be in its calcium replete conformation to have appreciable binding to chondrocyte proteoglycans that have chondroitin sulfate side chains. Moreover, as demonstrated in Example 4, COMP is an adhesive protein for human chondrocytes with maximal adhesive activity in the calcium-replete form. Previous studies have reported either that chondrocytes did not adhere to COMP at all (Sommarin et al., 1989; Oldberg et al., 1992) or that appreciable attachment could be observed only at very high COMP concentration (DiCesare et al., 1994). COMP's ability to support cell attachment was assessed in a short term attachment assay, as well as whether the type 3 conformation could have any effect on its adhesive activity.

A chondrocyte-derived cell line, TC1a, was used to test whether COMP is an adhesive protein. Cells grown both in monolayer and alginate culture systems were used for the assays.

Figure 4:
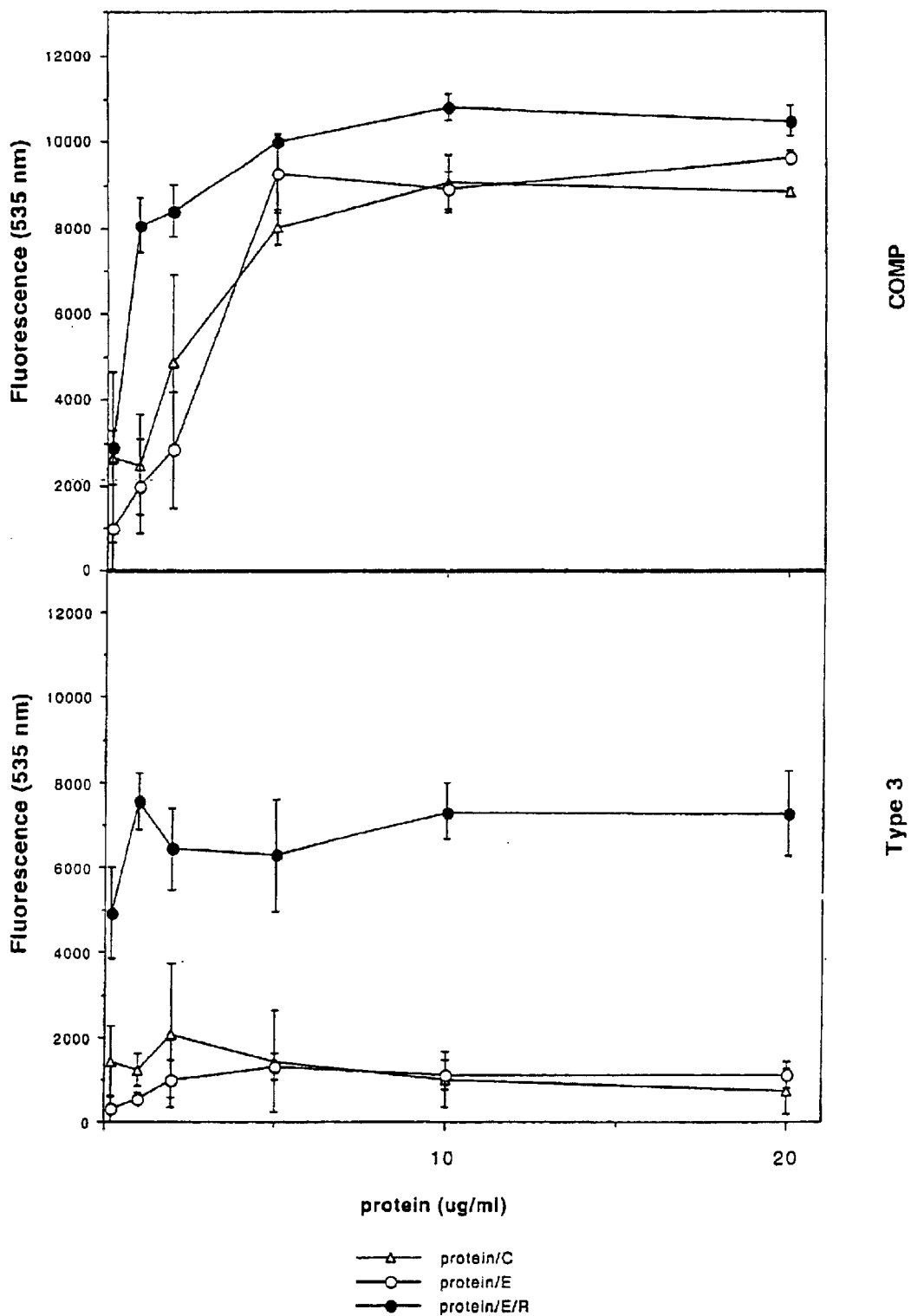
FIG. 4 depicts attachment of chondrocyte-derived cell line TC1a cultured in monolayer to COMP or to a fusion protein comprising the type 3 repeats of COMP. COMP (top column) or type 3 repeats fusion protein (bottom column) in the presence of $CaCl_2$ (/C, triangle) or EDTA (/E, open circle) or in the presence of EDTA and treated with DTT (/E/R, solid circles). Attachment assays were carried out. Results are shown as mean±standard deviation of quadruplicate experiments.

For TC1a cells grown in monolayer, hCOMP in a calcium replete conformation supported cell attachment in a dose-dependent manner (FIG. 4). At protein coating concentrations of 5 µg/ml and higher, cells also spread on the protein-coated wells. Treating hCOMP with EDTA before coating had no obvious effect on attachment (FIG. 4). According to previous reports, reduction of TSP1 and TSP2 helps to expose the RGD sequences which are possibly cryptic inside the complex intracellular disulfide bonds within the type 3 calcium-binding repeats (Sun et al., 1992; Chen et al., 1994). This was tested for hCOMP, in view of the high degree of homology in the type 3 repeats among all TSPs and the presence of the RGD sequence in hCOMP. Indeed, reduction of hCOMP after coating increased its adhesive activity, especially at low COMP coating concentration (FIG. 4). Cells attached to and spread on dithiothreitol-treated COMP coated at 1 µg/ml. To identify to which region(s) of COMP cells attach, the adhesive activities of three different fusion proteins, expressed in and purified from $E.\ coli$, were tested. The fusion proteins were produced by expression from pGEX vectors (Amersham Pharmacia Biotech, Uppsala) with insertions such that the fusion proteins comprise glutathione S-transferase of $Schistosoma\ japonicum$ and either the type 2 repeat region of COMP ($Leu_{88}$-$Arg_{268}$), the type 3 repeat region of COMP ($Arg_{268}$- $Ile_{517}$), or the COOH-terminal region of COMP ($Asp_{518}$-$Ala_{757}$). TC1a cells failed to show significant attachment to any of these recombinant fusion proteins. However, when the type 3 repeat fusion protein was reduced after coating, cells were able to attach and spread well on the plate. RGD peptide effectively inhibited the attachment of TC1a cells to hCOMP. These data indicate that COMP is an adhesive protein and that the type 3 repeats are in part responsible for this adhesive activity, possibly through the RGD sequence.

Figure 5:
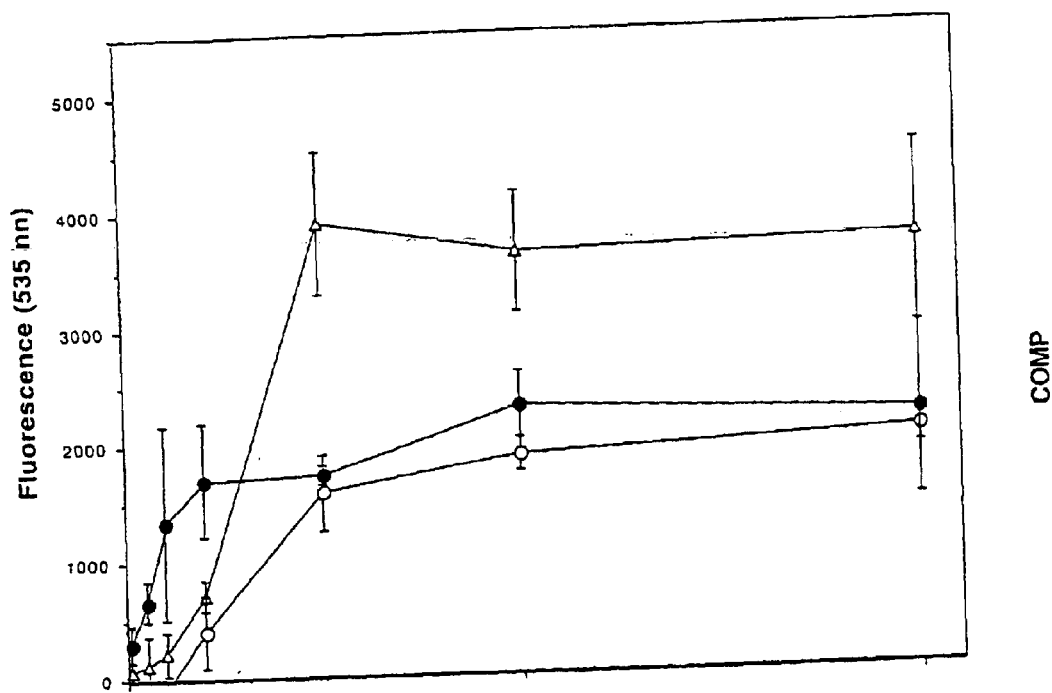
FIG. 5 depicts attachment of chondrocyte-derived cell line TC1 a after alginate culture to COMP. Results are shown as mean±standard deviation of a quadruplicate experiment.

When chondrocytes are cultured in monolayer, they dedifferentiate with time and lose some of the characteristics of chondrocytes (von der Mark et al., 1977). After prolonged culture in monolayer, chrondrocytes switch from a differentiated phenotype that produces type II collagen and abundant proteoglycans to a de-differentiated fibroblastic phenotype that produces type I collagen and less proteoglycans. This de-differentiated process can be reversed by culturing the chondrocytes in suspension, e.g., in alginate culture system (Robbins and Goldring, 1998; Goldring, 1998; Hauselmann et al., 1994; Bonaventure et al., 1994). To address this problem, the alginate system was adopted to re-differentiate the TC1a cells and to test hCOMP's support of attachment of these re-differentiated cells. Wild type hCOMP in a calcium replete form was also able to support attachment of TC1a cells after 7- to 10-day culture in alginate beads (FIG. 5). Chelation of calcium before coating decreased the level of attachment by approximately 50% (FIG. 5). These data suggest that the calcium replete wild type conformation of hCOMP is required for supporting maximal attachment of differentiated TC1a cells cultured in alginate system. This finding also explains the previous controversy on the adhesive activity of COMP. When COMP was purified in the calcium-depleted conformation, its adhesive activity is low for chondrocytes isolated from tissues which are in a differentiated state (Sommarin et al., 1989; Oldberg et al., 1992; DiCesare et al., 1994).

COMP is shown to behave differently when it is purified in a calcium replete form as compared to previous reports when it was purified in the presence of EDTA (Rosenberg et al., 1998; Hauser et al., 1995; Morgelin et al., 1992; DiCesare et al., 1994). These results demonstrate that calcium-binding is critical for maintaining the correct structural conformation of COMP, which in turn is critical for its functions, including its optimal GAG-binding properties and its ability to support cell attachment.

Furthermore, as discussed in Example 5, COMP is a motility factor for chondrocyte migration. Human costochondral cartilage cells were used to test if COMP is active in promoting chondrocyte migration. COMP, as well as TSP1 and Vitrogen (Cohesion; Palo Alto, Calif.), at different concentrations, was coated on the underside of membranes of transwell migration assay wells. Chondrocyte cells, prepared as in the attachment assays, were loaded into the wells. Migration was allowed to go on at 37° C. for four hours. Nonmigratory cells remaining inside the wells were removed with cotton swabs. Cells which migrated to the underside of the membranes were quantified using a CyQuant kit.

Figure 6:
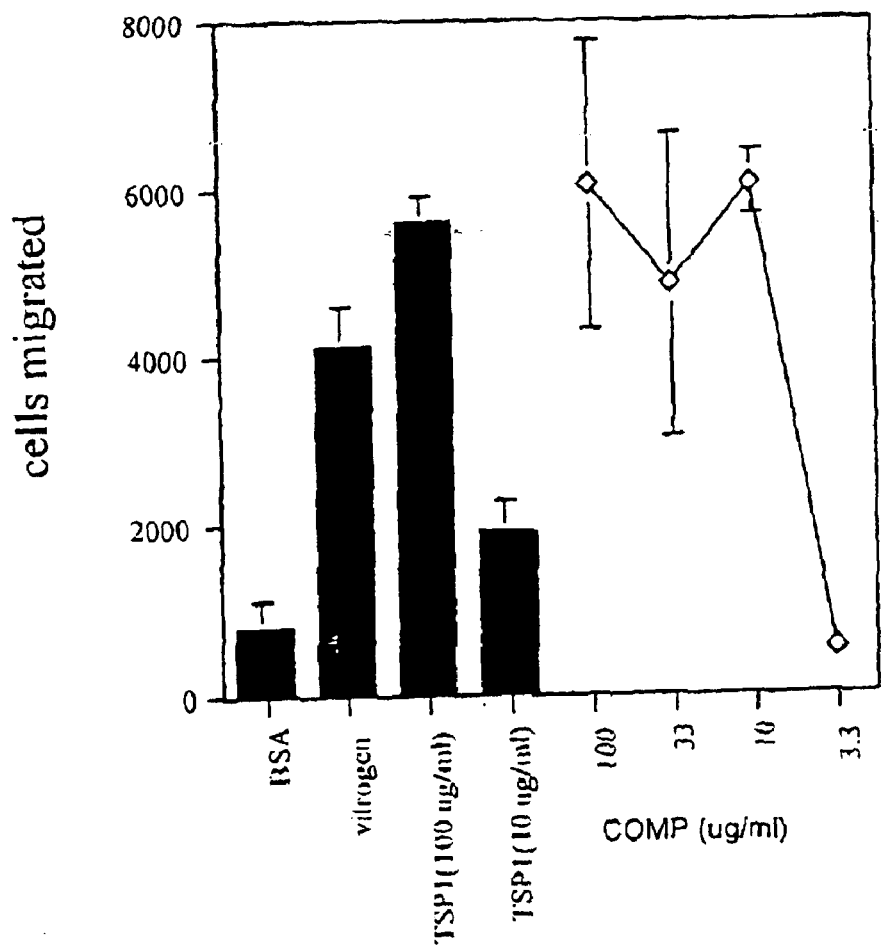
FIG. 6 depicts migration of chondrocytes towards COMP. COMP, TSP1, or Vitrogen (Cohesion; Palo Alto, Calif.) are coated at the underside of the transwell membranes. Chondrocytes that have migrated were quantified, and are represented here as mean±standard deviation.

The data (FIG. 6) show that COMP is a good chemoattractant for chondrocyte migration. COMP coated on the underside of the membrane, as low as 10 mg/ml, promoted the chondrocytes to migrate towards it. TSP1 also promotes chondrocyte migration. However, at the same concentration of 10 mg/ml, COMP seems to be a more potent chemoattractant than TSP1. Vitrogen (Cohesion; Palo Alto, Calif.), which is virtually collagen, also promoted chondrocyte migration, in agreement with previous reports. (Shimizu, M., K. Minakuchi, S. Kaji, and J. Koga, "Chondrocyte migration to fibronectin, type I collagen, and type II collagen," Cell Structure & Function, 22:309–315 (1997)).

These data, along with data that COMP supports attachment of chondrocytes, suggest that COMP is a good candidate for inclusion in an artificial matrix for cartilage repair. COMP in the artificial matrix can serve as a good chemoattractant for the chondrogenic cells to migrate into the matrix, and serves as a good attachment factor. In addition, with bound vitamin $D_3$, its metabolites or retinoic acids, COMP can help to further promote chondrocyte differentiation, and make the right type of extracellular matrix.

The research discussed herein has provided several important observations about the structure and function of COMP. Compared to the original method of COMP purification, recombinantly expressed and purified hCOMP discussed herein has several unsurpassed advantages. This is the first time when a human COMP can be purified in an unlimited quantity if adapted to a scale-up culture. In this novel approach to purification, calcium is kept present throughout the procedure to maintain calcium-dependent structures. This approach is based on the fact that during biosynthesis and in the extracellular environment, COMP should be in the presence of millimolar levels of calcium. Up until now, the most widely available COMP was purified from bovine cartilage or rat fibrosarcoma cells because of their availability. However, bovine or rat materials cannot be used for humans because of the immune response they can potentially provoke. Human COMP has also been reported to be purified from human cartilage (DiCesare et al., 1995; Neidhart et al., 1977). However, the source of human material is limited. Additionally, the methods of reported COMP purification also set limits of its usefulness. There were two published methods in purifying COMP. The earliest method was by extraction with a solution containing guanidine HCl and EDTA (Hedbom et al., 1992). This effectively denatures proteins. The second method was the purifying of COMP in a "native" state. However, this method utilized EDTA extraction. EDTA treatment chelates calcium and/or other divalent cations from COMP and renders it in a calcium depleted form. There has been data showing that this conformational change may be irreversible, since COMP thus purified did not fold into a compact calcium replete form under EM in the presence of calcium. COMP purified in the presence of EDTA has been reported to be incapable of performing several functions compared to its counterpart purified in the calcium replete form as disclosed herein. For example, COMP was reported to be unable to bind to heparin-Sepharose, and it has been controversial as to whether COMP can support the attachment of chondrocytes. As has been shown in the Examples described herein, being in a calcium replete form is critical for COMP's maximal GAG binding capacity and maximal cell adhesive activity.

1. Purified COMP

The invention includes purified cartilage oligomeric matrix protein (COMP), such as human COMP (hCOMP), including hCOMP prepared by expressing and/or purifying hCOMP in the presence of calcium, and methods of purifying COMP (e.g., hCOMP) in the presence of calcium. The COMP can be purified in a high-calcium concentration environment, for example, where calcium is present at a millimolar range (level), e.g. at least 300 $\mu$M (0.3 millimoles). As used herein, "calcium-replete conditions" refers to a calcium concentration of at least 0.3 millimoles. In one embodiment, hCOMP clones can be introduced into cells, for example, cells capable of expressing and secreting hCOMP; the cells are cultured, e.g. in a medium under conditions suitable for expressing the hCOMP; and the hCOMP are purified in the presence of calcium. The hCOMP clones can be produced by cloning full length hCOMP. Recombinant techniques are well-known to those of skill in the art. See, for example, Ausubel, F. N. et al., *Current Protocols in Molecular Biology*, Greene Publishing Assoc. and John Wiley & Sons, Inc. (1998). Methods of introducing a protein such as hCOMP into a cell include, but are not limited to, transfection, transformation and electroporation. Conditions suitable for expression are also well known in the art. The cells can be cultured in a calcium-replete culture medium. The hCOMP can be expressed and/or purified in a solution an environment at millimolar levels (e.g. characterized by a calcium concentration of at least 300 $\mu$M). Cells capable of expressing COMP include some fibroblasts, chondrocytes, tendon, ligament, smooth muscle cells, pericytes, and human embryonic kidney cells or other cells transfected with COMP DNA (DNA encoding COMP), for example.

Also encompassed is COMP purified in different concentrations of calcium. Such COMP may be cleaved differently by trypsin. In one embodiment, hCOMP produced by the methods herein digests into bands of 50 kDa or 55 kDa when cleaved by trypsin. In another, purified hCOMP which digests into bands of 62 kDa or 67 kDa when cleaved by trypsin.

Fragments, mutations and other derivatives and analogs of COMP (e.g. human COMP, such as hCOMP purified by the methods described herein) are also encompassed within the invention, as well as methods of making and using such fragments, mutations and other derivatives and analogs. In one embodiment, such derivatives include the binding sites (e.g. the calcium binding sites) of COMP, particularly COMP in its calcium-replete conformation. As used herein, "calcium-replete conformation" refers to the form of COMP which has been purified under calcium-replete conditions. Also included are compositions which include COMP and/or a COMP derivative.

2. Anti-COMP Antibodies and Elisa Kits

The invention also encompasses antibodies to COMP (including hCOMP) purified in the presence of calcium, for example, hCOMP purified under the methods disclosed herein. The anti-COMP antibodies can be monoclonal or polyclonal. They can be chimeric. They can be antibodies specific to COMP derivatives, such as COMP fragments or mutants. They can be antibodies which bind to degraded COMP, including COMP fragments) and which do not bind to non-degraded COMP. Alternatively, they can bind to non-degraded (intact, full-length) COMP, but not to degraded COMP. Methods of making antibodies are well-known in the art. In one embodiment, the antibody is to purified hCOMP which is prepared by introducing hCOMP clones into cells capable of expressing and secreting hCOMP, culturing the cells in a culture medium under conditions suitable for expressing the hCOMP; and purifying the hCOMP in the presence of calcium. In one embodiment, the antibody is an antibody to the hCOMP purified in a calcium-replete environment, for example, where calcium is present at a millimolar range (level), e.g. at least 300 $\mu$M (or 0.3 millimoles). Also encompassed in the invention is fragments of the antibodies described herein. As used herein, "antibody" can refer to a type of antibody, as for example, one monoclonal antibody of a certain specificity and affinity, or a preparation of polyclonal antibodies in an antiserum, or a quantity of antibodies in an assay, for example, so that the term "antibody" includes plural meanings.

The invention also encompasses ELISA kits comprising purified hCOMP and/or antibodies to such hCOMP which is prepared by introducing hCOMP clones into cells capable of expressing and secreting hCOMP, culturing the cells in a culture medium under conditions suitable for expressing the hCOMP; and purifying the hCOMP in the presence of calcium.

3. The Use of COMP as a Marker in Destructive Joint Diseases

In one embodiment, COMP is used as a marker in destructive joint diseases. Osteoarthritis (OA) and rheumatoid arthritis (RA) of the joints are common causes of pain and disability in the adult population. In these inflammatory and mechanical joint diseases, cartilage matrix turnover goes into negative balances, resulting in the progressive destruction of articular cartilage with varying degrees of destruction of the bone. OA is a slowly evolving process from the initiation of joint damage to further degradation. The clinical diagnosis of OA is based on a history of joint pain and radiographic finding. Normally at the stage of diagnosis, tissue destruction is already advanced and patients need surgery. Recently, aggressive early pharmacotherapy has targeted RA in the hope that this may arrest or delay disease progression and improve ultimate outcome. This early aggressive treatment is only warranted if the disease has severe prognosis. Therefore, simple and non-invasive and reliable method for detecting sub-clinical arthritis and for assessing disease progression prognosis will be of great value.

In human synovial fluid (SF) and serum, increased amounts of COMP have been reported after knee injury. In early-stage OA, elevated COMP levels in serum and SF have been observed (Neidhart et al., 1997; Petersson et al., 1998a; Petersson et al., 1998b). In patients with chronic knee joint pain, an elevated level of COMP has been correlated with subsequent radiographic detection of OA, whereas the COMP level remains unchanged in patients with normal radiographs at follow-up (Petersson et al., 1998a; Petersson et al., 1998b). In the case of traumatic knee injury, some patients who develop anti-COMP auto-antibodies have an increased risk for developing post-traumatic osteoarthritis (Kuhne et al., 1998). COMP level is also increased in the early stage of RA patients who have aggressive RA and who subsequently develop advanced large-joint destruction (Saxne et al., 1993; Forslind et al., 1992; Wollheim et al., 1997). Subsequently, with advanced RA, COMP level is decreased. However, in SF, a high percentage of RA patients (84%) and other inflammatory arthritis (60%) patients show a high degree of COMP degradation (Neidhart et al., 1997). In summary, increased serum COMP concentration can be used as an effective predictive marker in the early stages of OA and RA. An additional criterion of increased degradation of COMP in SF can be used as a marker for RA and other inflammatory joint diseases.

Standard techniques for the assays described herein are well-known. (See Ausubel, supra). For example, the methods can be performed the same as or similar to the methods described in patent application WO 98/07035, filed Aug. 8, 1997.

It has been shown that the COMP level in serum has a positive correlation with the COMP level in SF. Sera can easily be obtained non-invasively and with little pain from patients and COMP levels in the sera can easily be measured by competitive enzyme-linked-immunosorbent assay (ELISA). So far, a diagnostic kit has not been developed, probably due to the limited source of hCOMP and its antibodies. Using the methods of purifying COMP provided herein, large amounts of COMP can be purified in the presence of calcium, preferably under calcium-replete conditions. Antibodies to such hCOMP can also be included. Competitive ELISA using COMP purified as described herein can be carried out, for example, on a plate, which can be a 96-well microtiter plate or other substrate suitable for the attachment of proteins. Human COMP is preferred over COMP purified from other animal sources for use in this ELISA assay and kit, since it has been shown that ELISA using bovine COMP gives inaccurate measurements (Neidhart et al., 1997). In the ELISA assay, the plate can be coated with 1 $\mu$g/ml purified hCOMP. Excess binding sites on the plate can be blocked, for example, with bovine serum albumin. Sera from patients can be serially diluted, and incubated with a specific anti-COMP antibody along with standard, i.e., known amounts of purified hCOMP, overnight at 4° C. The solutions are then added to the plate and incubated for one hour at room temperature. After washing, enzyme conjugated secondary antibodies can be added to the wells, and the assay can be carried out as a standard ELISA assay. COMP concentration in patient sera can be derived from the linear range of the standard curve and dilution factor. In this assay, preferably a monoclonal antibody will be used as the primary antibody. However, polyclonal antibodies can also be used. Polyclonal antibodies against COMP have been developed (Hecht et al., 1998), and monoclonal antibodies against COMP are being developed. An unlimited source of purified recombinant hCOMP can be provided using the techniques provided herein, for the development of this ELISA.

Standard ELISA assays can be used to detect whether patients with traumatic knee injuries display anti-COMP antibodies, for prognosis and treatment. In this assay, hCOMP is coated on a plate, which can be a 96-well microtiter plate or other suitable substrate, and serial dilutions of patient sera will be used to detect the presence of anti-COMP auto-antibodies. In this assay, hCOMP has great advantages over COMP from other animal sources, in that hCOMP should offer higher sensitivity and accuracy, due to the possibility that the auto-antibodies may recognize epitopes only present on human COMP.

Immunoblots can be used to detect if COMP in SF is degraded. Briefly, proteins in SF can be precipitated, for example, by ethanol. The precipitate will be resuspended in a solution containing SDS running buffer without reducing agent. The proteins can be separated, e.g., on a 3–15% polyacrylamide gel in SDS, and transferred electrophoretically onto a piece of nitrocellulose paper. COMP will be detected by standard immunoblot method using either polyclonal anti-COMP antibodies or a monoclonal antibody that recognizes both the non-degraded and degraded forms of COMP. The relative intensities of the bands will be scanned and the percentage of degraded bands will be calculated. Here, purified hCOMP and commercially available molecular mass standard can be used for identifying the intact and degraded forms of COMP.

4. The Use of COMP in Cartilage Repair

In the field of cartilage repair, focus has been on the transplantation of chondrocytes and mesenchymal stem cells, and transplantation of artificial matrices, or a combination of both. However, the outcomes are all short of being satisfactory, especially in long term follow-up. It is believed that the repaired tissue should have the same or similar composition and structure of hyaline cartilage for it to stand the test of time and usage. Therefore, the histological properties of the repaired tissue is an important criterion in judging how adequate a repair procedure is and how well the outcome will be. In hyaline cartilage, the major components are type II collagen and the large aggregating proteoglycan aggrecan. In long term follow-up, the main problem of many cartilage repair procedures is that the repaired tissue is fibrous cartilage that contains more type I collagen instead of type II collagen, and fewer proteoglycans compared to hyaline cartilage. Fibrous repair tend to deteriorate after a certain period. Previous research has shown that the ability of the chondrocytes to produce these proteins depends on the differentiation state of the cells. COMP can play an important role in solving this problem.

Vitamin $D_3$ and retinoic acid have been shown to be important during the morphogenesis and repair of cartilage and bone. Retinoic acid has the ability to influence limb formation and to stimulate matrix calcification and collagen synthesis in weight-bearing growth chondrocytes. Vitamin $D_3$ and its two major active forms of metabolite, 1,25-dihydroxyvitamin $D_3$ [1,25(OH)$_2$D$_3$], and 24R, 25-dihydroxyvitamin $D_3$[24R, 25(OH)$_2$D$_3$], are found to be essential for normal chondrocyte development and differentiation. The metabolite promotes mesenchymal cell differentiation into chondrocytes and chondrocyte differentiation towards the morphologically hypertrophic phenotype. 1,25 (OH)$_2$D$_3$ specifically stimulates transcription of collagen type II and increases morphological chondrogenesis in limb-bud mesenchymal cells. The regulatory activity of retinoic acid has been partially attributed to the stimulation of bone morphogenetic protein-7 levels, which in turn stimulated maturation of chondrocytes (Grimsrud et al., 1998). The effects of vitamin $D_3$ metabolites have been through regulation of the intracellular signaling pathways involving cAMP and protein kinase C (Schwartz et al., 1998a; Schwartz et al., 1998b).

Vitamin $D_3$ metabolites and retinoic acid are basically insoluble in aqueous solution and need carrier protein for their transport and storage under physiological conditions. COMP has been recently reported to be a naturally occurring binding protein (Guo et al., 1998). Thus, COMP can function as a storage and delivery protein for these signaling molecules.

Besides retinoic acid and vitamin $D_3$ metabolites, COMP has been shown to also bind to collagen (Rosenberg et al., 1998). From our studies, COMP binds to different GAGs found in chondrocytes, is an adhesive protein for both de-differentiated and differentiated chondrocytes, and can serve as a chemoattractant for chondrocyte migration. The Examples herein demonstrate that the calcium-replete conformation of COMP is pivotal for it to exert is maximal GAG-binding and cell-attachment supporting activities. These properties of COMP make it an ideal candidate as a useful cartilage repair agent.

COMP can be used in various procedures of cartilage repair, both as a motility factor (e.g., a chemoattractant) and an adhesive factor for chondrocytes or mesenchymal cells and also as a differentiation factor (with its bound retinoic acid or vitamin $D_3$ metabolites).

For example, autologous chondrocyte transplantation has become a popular surgical treatment for full-thickness cartilage defect in the knee. This procedure showed a promising outcome, but long term deterioration can be a problem (Koh et al., 1998; Brittberg et al., 1990; Brittberg, et al., 1994). The procedure involves the isolation of patient chondrocytes, in vitro expansion of the chondrocytes, and injection of the cultured chondrocytes into the area of the defect, covered by a sutured periosteal flap taken from proximal medial tibia. This procedure utilizes an in vitro culture of chondrocytes in monolayer. As reported before, in monolayer cultures, chondrocytes tend to de-differentiate with time in culture. The dedifferentiated chondrocytes switch from a type II collagen expression phenotype to a type I collagen expression, and less aggrecan producing, fibroblast-like phenotype.

For example, COMP, e.g. hCOMP purified as described herein, can be used in methods of transplanting chondrogenic cells comprising culturing the cells in the presence of COMP. As used herein, "chondrogenic cells" mean cells capable of producing cartilage, including chondrocytes and mesenchymal stem cells. The chondrogenic cells can be autologous. As used herein, "autologous" means that the cells are from the same individual into which they will be transplanted. The COMP can be bound with a differentiation agent. The differentiation agent can be vitamin $D_3$ or a vitamin $D_3$ metabolite or retinoic acid. The cells can be isolated from an individual, for example, a animal, such as a mammal, e.g. a human (for example, a patient). The hCOMP can mediate attachment of cells (e.g. expanded chondrocytes) and provide delivery to the cells of the differentiation agent and release of the differentiation agent. The cells can be cultured on tissue culture plates coated with hCOMP bound with a differentiation agent. The cells, e.g. chondrocytes and mesenchymal stem cells, can be injected into the defect area, in the presence of hCOMP, where hCOMP is either alone or with a bound differentiation agent, thereby aiding in the maintenance of differentiated chondrocytes and stimulating production of type I collagen and other cartilage components by the chondrocytes in the defect areas. The cells can be cultured in the presence of hCOMP (which can be bound with a differentiation agent). The hCOMP can be purified by the methods described herein. The invention also encompasses producing chondrocytes for autologous transplantation using these methods, and the chondrocytes produced by these methods. In one embodiment, the chondrocytes can be cultured on tissue culture plates coated with COMP with bound vitamin $D_3$ metabolites. Here, COMP acts as an attachment factor and also provides the differentiating factor. The expanded chondrocytes will also be injected in the presence of COMP with bound vitamin $D_3$ metabolites into the defect area. This should also help to maintain the differentiation stage of the chondrocytes and stimulate the production of type II collagen by the chondrocytes in the defect. Human COMP is preferable to COMP from other animal sources to avoid the potential problem of host immune response.

Another research focus is on the development of artificial matrices for cartilage repair. Artificial matrices can serve both as a method of delivering and stabilizing of cells and reagents in defects, and in some cases, these matrices may also serve to allow or stimulate ingrowth of host cells and matrix formation as well as the binding of new cells and matrix to host tissue (Buckwalter and Mankin, 1998; Silver and Glasgold, 1995; Newman, 1998). Artificial matrices include a variety of biological and nonbiological materials, including treated cartilage and bone matrices, collagens, collagens and hyaluronan, fibrin gels, carbon fibers, porous polylactic acid, etc. Different matrices have been developed by different laboratories and each has its own advantages and shortcomings. The criteria for judging an implant are that it provides a porous structure that cells can migrate to, adhere to and grow, that it promotes and maintains the seeded cells their differentiated chondrocyte phenotype, and that it does not provoke inflammation or toxicity in vivo. In artificial matrices, growth factors that can simulate chondrocyte growth and differentiation can also be used, including, for instance, insulin-like growth factor, fibroblast growth factor, transforming growth factors, and bone morphogenic proteins, in repairing and regenerating articular cartilage. However, their multiple effects on numerous tissues other than cartilage, and the limited understanding of their effects in vivo, have made researchers cautious about their use in the clinic. There has not been any report on the use of COMP in the implant, because of the limited knowledge of COMP up until now.

The invention includes implants for cartilage repair. As used herein "implant" refers to a composition which can be implanted into an individual. "Repair" means to improve or return partially or completely to an undamaged state.

In a preferred embodiment, collagen gels, such as type I collagen and a type II collagen are used for the matrix.

Studies have shown that type II collagen with seeded chondrocytes has advantages over the type I collagen implants in that it shows better maintenance of the chondrocyte phenotype and matrix synthesis (Nehrer et al., 1997). In one embodiment, COMP, bound with a differentiation agent such as vitamin $D_3$ or its metabolites or retinoic acid, is added to the type II collagen gel as an implant. Proteoglycans, including chondroitin sulfate proteoglycans, can also be included in the gel. Mesenchymal stem cells from blood or bone marrow can replace chondrocytes because they are relatively easy to obtain. In this transplant, hCOMP, by virtue of its GAG and collagen binding activity and its pentameric structure, can act as a bridge between the collagen fibers and proteoglycans for better incorporation of the matrix. COMP can also serve as an adhesive material for the seeded chondrocytes or mesenchymal stem cells. In cases where cells are not included in the matrix, COMP can serve as a motility factor for cells to move into the matrix. Since vitamin $D_3$ can be bound to COMP before COMP is put into the matrix, COMP also serves as a delivering and slow releasing mechanism for this differentiation agent and helps to maintain and promote the chondrocyte or mesenchymal cells to mature and differentiate, thereby producing the type of cartilage matrix found in an individual who has not experienced trauma, pathology or other damage to the cartilage. Such cartilage is referenced herein as naturally occurring non-traumatic cartilage (i.e., "normal" cartilage).

EXAMPLES

Example 1

Expression and Purification of Human COMP (HCOMP)

DNA encoding full length human COMP (Newton et al., 1994) was cloned into pcDNA3.1+vectors (Invitrogen, Carlsbad, Calif.). The resulting clone was transfected into human embryonic kidney cells (293 cells) using Lipofectin reagent (Life Technologies, Gaithersburg, Md.). Single colonies of stable transfectants were isolated under the selection of G418 and expanded. Cells were grown in Dulbecco's modified Eagle's medium (DME) (Life Technologies) plus 10% fetal bovine serum (FBS) until nearly confluent. Cells were then washed twice with DME and grown in DME plus 2 mM L-glutamine for 48 hours. Conditioned medium was collected for purification. To purify hCOMP, conditioned medium was loaded over a heparin-Sepharose column, and washed extensively with Tris-buffered saline (TBS) containing >2 mM $CaCl_2$. The bound material was then eluted from the column by high salt solution with NaCl concentration greater than 0.5 M buffered in 10 mM Tris, pH 7.5, containing 2 mM $CaCl_2$. Alternatively, the conditioned medium was precipitated by 30% ammonium sulfate at 4° C. overnight. Precipitates were resuspended in TBS containing 2 mM $CaCl_2$ and loaded onto a linear 10–20% sucrose gradient in TBS with 2 mM $CaCl_2$ and separated by centrifugation in a Beckman SW41 Ti rotor at 38,000 rpm for 20–24 hours. Fractions containing COMP were pooled. Fractions were stored at −80° C. until further use.

When human embryonic kidney 293 cells were transfected with full length human COMP cDNA, they were able to process and secrete hCOMP (FIG. 1). The secreted and purified hCOMP is a pentamer. Untransfected 293 cells did not synthesize any endogenous COMP as judged by immunoblot with polyclonal antibodies against COMP, F8 (Hecht et al., 1998). The purified protein comigrated in SDS-PAGE with COMP from human cartilage and tendon.

Example 2

Analysis of COMP as a Calcium-Binding Protein

According to the presence of the type 3 repeats in COMP and studies on TSP1, COMP is predicted to bind calcium. However, COMP, originally purified in the presence of EDTA, did not bind calcium, and failed to show a significant conformational difference as a function of calcium (Rosenberg et al., 1998; Hauser et al., 1995; Mörgelin et al., 1992; DiCesare et al., 1994). Direct calcium binding, rotary shadowing electron microscopy (EM) and limited trypsin digestion were used to show that COMP is a calcium binding protein and displays different conformation under different calcium concentrations Purified COMP in Tris-buffered saline containing 2 mM $CaCl_2$ was diluted with 70% glycerol, 0.15 M ammonium acetate and 0.2 mM $CaCl_2$. Equivalent samples of protein were adjusted to 5 mM EDTA prior to mixing with 70% glycerol and 0.15 M ammonium acetate prepared without $CaCl_2$. The samples were then sprayed onto freshly cleaved mica and rotary-shadowed with platinum. The rotary shadowing EM images (FIG. 2) of hCOMP show that the recombinant hCOMP is a pentamer. In the presence of calcium, hCOMP had a compact appearance that made it difficult to resolve the five subunits. In the presence of EDTA, hCOMP adopted an extended conformation. The uncorrected lengths of the arms of hCOMP from the interchain disulfides to the end of the C-globe were 19.9±2.6 nm in the presence of calcium and 30.4±3.3 nm in the presence of EDTA (mean±std of 20 measurements each). These results suggested that hCOMP, when purified in a calcium replete form, will undergo conformational changes when calcium is chelated from the molecules.

Limited trypsin digestion of hCOMP was employed under various calcium concentrations. Six tryptic fragments with the molecular mass of 27, 36, 50, 55, 62 and 67 kDa were observed in the digestion of hCOMP. At low calcium concentrations (in the range of 1–25 $\mu M$), hCOMP was readily cleaved by trypsin into two small fragments at 27 kDa and 36 kDa (FIG. 3). Purified recombinant COMP was dialyzed against Tris-buffered saline containing either 2 mM or 0.5 mM $CaCl_2$. EDTA was added to 16 $\mu g$ of each protein so that the final free $Ca^{2+}$ concentrations were as indicated in $\mu M$. Trypsin digestion was carried out at an enzyme:substrate ratio of 1:100 for 20 hrs at 0° C. Digestion was stopped by adding reducing SDS sample buffer and the polypeptides were separated by SDS-PAGE. When the calcium concentration increased to the range of 50–100 $\mu M$, hCOMP was digested into intermediate bands at 50 kDa and 55 kDa. When calcium concentration was higher than 150 $\mu M$, with increasing calcium concentration, the 62 kDa and 67 kDa bands of hCOMP started to appear. The 67 kDa band became the prevalent band at calcium concentrations in the mM (millimolar) range. This band is not present in mutants of hCOMP that affect its calcium binding ability.

Direct calcium binding to COMP was measured by equilibrium dialysis using $^{45}CaCl_2$. Briefly, TSP1 and COMP were dialyzed in Slide-A-Lyzer dialysis units (Pierce, Rockford, Ill.) against dialysis buffer containing 0.3 mM $CaCl_2$ and 10 mCi/ml of $^{45}CaCl_2$. At the end of dialysis, 10 ml of protein sample and dialysis buffer were taken out for scintillation counting and protein determination. The number of calcium ions bound was calculated. At 0.3 mM free calcium concentration, each TSP1 subunit bound 10±2 calcium ions (mean±SD of four data points). This is in agreement with previous reports where 11–12 calcium ions were reported to bind to each TSP1 subunit (Lawler and Simons, 1983; Misenheimer and Mosher, 1995). Under the same conditions, each subunit of COMP bound 11±1 calcium ions. This is the first time it is shown that COMP binds calcium ions, and the result is consistent with the presence of highly homologous type 3 calcium binding repeats in COMP and other TSP family members.

Example 3

Analysis of COMP as a Glycosaminoglycan (GAG) Binding Protein

To probe whether hCOMP could be a GAG-binding protein despite its lack of the $NH_2$-terminal heparin binding domain, and whether the conformation of the type 3 calcium-binding repeats could affect functions of hCOMP, we tested the interaction of hCOMP with common GAGs found in cartilage in the presence of either calcium or EDTA.

Affinity co-electrophoresis (ACE) (San Antonio et al., 1993) was used to quantify the binding of hCOMP to heparin and other commercially available GAGs derived from tissue sources, including chondroitin sulfates from cartilage, and values of $K_d$ were measured. The results of these analyses are presented in Table 1. COMP bound low molecular weight heparin with a $K_d$ of 89 nM. This is in agreement with our observation that hCOMP binds to heparin-Sepharose. While binding to heparin may suggest the presence of functional GAG-binding sites in COMP, heparin is a highly sulfated form of HS (heparan sulfate) that is made only in mast cells, and therefore is not truly representative of GAGs from most tissues. To better ascertain potential roles of GAGs and proteoglycans in COMP function, heparan sulfate, keratan sulfate, and three chondroitin sulfates (chondroitin-6-sulfate, C6S; chondroitin-4-sulfate; C4S; and dermatan sulfate, DS) were tested for binding to hCOMP in the presence of 2 mM calcium using ACE (Table 1). The data revealed that hCOMP bound to the three chondroitin sulfates with comparable affinities, with $K_d$s ranging from 328 to 583 nM, while binding to HS was weaker (1.2 $\mu$M). hCOMP did not bind to keratan sulfate.

To further determine whether the conformation of the calcium-binding type 3 repeats was critical to GAG binding, hCOMP was tested for binding to heparin and C6S in the presence of 5 mM EDTA. These results demonstrated that depletion of calcium reduced hCOMP binding to GAGs. While heparin binding was reduced only 3- to 5- fold by EDTA treatment, C6S binding appeared to be abolished by this treatment.

Example 4

Analysis of COMP as an Adhesive Protein

A chondrocyte-derived cell line, TC1a, was used to test whether COMP is an adhesive protein. Cells grown both in monolayer and alginate culture systems were used for the assays.

To prepare cells grown in monolayer for attachment assays, cells grown in 10 cm tissue culture plates were washed twice with HEPES buffered saline (HBS), and treated with 1 ml of 0.1 mg/ml TPCK-treated trypsin (Worthington, Lakewood, N.J.) in HBS at 37° C. for 5 minutes. Trypsinization was stopped with 2 ml of 0.5 mg/ml soybean trypsin inhibitor (Sigma) in HBS with 1 mM $CaCl_2$ (HBS/C). Cells were flushed off the plate as a single cell suspension, sedimented and washed twice with trypsin inhibitor solution. Subsequently, cells were resuspended in HBS/C containing 1% heat-inactivated bovine serum albumin (HI-BSA) at a final concentration of $2$–$2.5 \times 10^5$ cells/ml and used for attachment assays.

An alginate culture system was used to re-differentiate the chondrocytes as described (Robbins and Goldring, 1998; Goldring, 1998; Hauselmann et al., 1994; Bonaventure et al., 1994). Briefly, cells in monolayer culture were trypsinized and washed with phosphate buffered saline. Cells were resuspended in 1.2% solution of Keltone, LVCR alginate (Monsanto, St. Louis, Mo.) in 0.15 M NaCl at a final concentration of $4 \times 10^6$ cells/ml. The cell suspension was then passed through a 22 Gauge needle into 102 mM $CaCl_2$. Ten minutes after instant gelation, beads were washed with 0.15 M NaCl, and cultured in 1:1 DME/F-12 containing 10% FBS and 25 $\mu$g/ml ascorbate. To prepare cells in the alginate culture system for attachment assays, 7- to 10-day alginate bead cultures were solubilized with 55 mM citrate/0.15 M NaCl, pH 6.0 solution as described (Robbins and Goldring, 1998). Released cells were washed once with PBS and once with HBS/C before they were resuspended in HBS/C containing 1% BSA at a final concentration of $2$–$2.5 \times 10^5$ cells/ml.

Immulon II 96-well plates (DYNEX, Chantilly, Va.) were coated with COMP at various concentrations in HBS/C or HBS containing 5 mM EDTA (HBS/E) at 4° C. overnight. The plates were then blocked with 1% HI-BSA in HBS/C or HBS/E, respectively, for 30 minutes at 37° C. After blocking, some wells coated with proteins in HBS/E were reduced with 20 mM dithiothreitol (DTT) in HBS/E for 30 minutes at 22° C. Wells were washed 4 times with HBS/C before addition of 100 $\mu$l of cells to each well and incubated for 2 hours at 37° C. At the end of the incubation, after examination under phase contrast microscopy, the plate was washed 3 times with HBS/C. The amount of cells attached to each well was quantified using CyQuant kit (Molecular Probes, Eugene, Oreg.).

For TC1a cells grown in monolayer, hCOMP in a calcium replete conformation supported cell attachment in a dose-dependent manner (FIG. 4). At protein coating concentrations of 5 $\mu$g/ml and higher, cells also spread on the protein-coated wells. Treating hCOMP with EDTA before coating had no obvious effect on attachment (FIG. 4). Reduction of hCOMP after coating increased its adhesive activity, especially at low COMP coating concentration (FIG. 4). Cells attached to and spread on dithiothreitol-treated COMP coated at 1 $\mu$g/ml. To identify to which region(s) of COMP cells attach, the adhesive activities of fusion proteins were tested. The fusion proteins were produced by expression from pGEX vectors (Amersham Pharmacia Biotech, Uppsala) with insertions such that the fusion proteins comprise glutathione S-transferase of *Schistosoma japonicum* and either the type 2 repeat region of COMP ($Leu_{88}$-$Arg_{268}$), the type 3 repeat region of COMP ($Arg_{268}$-$Ile_{517}$), or the COOH-terminal region of COMP ($Asp_{518}$-$Ala_{757}$). TC1a cells failed to show significant attachment to any of these recombinant fusion proteins. However, when the type 3 repeat fusion protein was reduced after coating, cells were able to attach and spread well on the plate (FIG. 4, not shown). RGD peptide effectively inhibited the attachment of TC1a cells to hCOMP.

The alginate system to re-differentiate the TC1a cells was adopted and the ability of hCOMP to support attachment of these re-differentiated cells was tested in the same manner as the monolayer cells. Wild type hCOMP in a calcium replete form was also able to support attachment of TC1a cells after 7- to 10-day culture in alginate beads (FIG. 5). Chelation of calcium before coating decreased the level of attachment by approximately 50% (FIG. 5). When COMP was purified in the calcium-depleted conformation, its adhesive activity is low for chondrocytes isolated from tissues which are in a differentiated state (Sommarin et al., 1989; Oldberg et al., 1992; DiCesare et al.,1994).

Example 5

Analysis of COMP as a Chemoattractant for Chondrocyte Migration

Human costochondral cartilage cells were used to test if COMP is active in promoting chondrocyte migration. COMP, as well as TSP1 and Vitrogen (Cohesion; Palo Alto, Calif.), at different concentrations, were coated on the underside of membranes of transwell migration assay wells (Costar, Cambridge, Mass.). Chondrocyte cells, prepared as in the attachment assays, were loaded into the wells. Migration was allowed to go on at 37° C. for four hours. Nonmigratory cells remaining inside the wells were removed with cotton swabs. Cells that migrated to the underside of the membranes were quantified using a CyQuant kit (Molecular Probes).

The data (FIG. 6) show that COMP is a good chemoattractant for chondrocyte migration. COMP coated on the underside of the membrane, as low as 10 µg/ml, promoted the chondrocytes to migrate towards it. TSP 1 also promoted chondrocyte migration. However, at the same concentration of 10 µg/ml, COMP appeared to be a more potent chemoattractant than TSP1. Vitrogen (Cohesion; Palo Alto, Calif.), which is virtually collagen, also promoted chondrocyte migration.

REFERENCES

Bonaventure, J., N. Kadhom, L. Cohen-Solal, K. H. Ng, J. Bourguignon, C. Lasselin, and P. Freisinger. 1994. Reexpression of cartilage-specific genes by dedifferentiated human articular chondrocytes cultured in alginate beads. *Exp. Cell Res.* 212:97–104.

Briggs, M. D., S. M. G. Hoffman, L. M. King, A. S. Olsen, H. mohrenweiser, J. G. Leroy, G. R. Mortier, D. L. Rimoin, R. S. Lachman, E. S. Gaines, J. A. Cekleniak, R. G. Knowlton, and D. H. Cohn. 1995. Pseudoachondroplasia and multiple epiphyseal dysplasia due to mutations in the cartilage oligomeric matrix protein gene. *Nat. Genet.* 10:330–336.

Brittberg, M., A. Lindahl, A. Nilsson, C. Ohlsson, O. Isaksson, and L. Peterson. 1994. Treatment of deep cartilage defects in the knee with autologous chondrocyte transplantation [see comments]. *N. Engl. J. Med.* 331:889–895.

Brittberg, M., A. Nilsson, A. Lindahl, C. Ohisson, and L. Peterson. 1996. Rabbit articular cartilage defects treated with autologous cultured chondrocytes. *Clin. Orthop.* 270–283.

Buckwalter, J. A. and H. J. Mankin. 1998. Articular cartilage repair and transplantation. *Arthritis Rheum.* 41:1331–1342.

Chen, H., J. Sottile, K. M. O'Rourke, V. M. Dixit, and D. F. Mosher. 1994. Properties of recombinant mouse thrombospondin 2 expressed in *Spodoptera cells. J. Biol. Chem.* 269:32226–32232.

DiCesare, P., N. Hauser, D. Lehman, S. Pasumarti, and M. Paulsson. 1994. Cartilage oligomeric matrix protein (COMP) is an abundant component of tendon. FEBS *Lett.* 354:237–240.

DiCesare, P. E., C. S. Carlson, E. S. Stollerman, F. S. Chen, M. Leslie, and R. Perris. 1997. Expression of cartilage oligomeric matrix protein by human synovium. FEBS Lett. 412:249–252.

DiCesare, P. E., M. Morgelin, C. S. Carlson, S. Pasumarti, and M. Paulsson. 1995. Cartilage oligomeric matrix protein: isolation and characterization from human articular cartilage. *Journal of Orthopaedics Research* 13:422–428.

DiCesare, P. E., M. Morgelin, K. Mann, and M. Paulsson. 1994. Cartilage oligomeric matrix protein and thrombospondin-1: Purification from articular cartilage, electron microscopic structure and chondrocyte binding. *Eur. J. Biochem.* 223:927–937.

Forslind, K., K. Eberhardt, A. Jonsson, and T. Saxne. 1992. Increased serum concentrations of cartilage oligomeric matrix protein. A prognostic marker in early rheumatoid arthritis. *Br. J. Rheumatol.* 31:593–598.

Goldring, M. B. 1998. Human chondrocyte cultures as models of cartilage-specific gene regulation. In Methods in Molecular Medicine: Human Cell Culture Protocals. G. E. Jones, editor. Humana Press Inc., Totowa, NJ.

Grimsrud, C. D., R. N. Rosier, J. E. Puzas, P. R. Reynolds, S. D. Reynolds, D. G. Hicks, and R. J. O'Keefe. 1998. Bone morphogenetic protein-7 in growth-plate chondrocytes: regulation by retinoic acid is dependent on the stage of chondrocyte maturation. *Journal of Orthopaedics Research* 16:247–255.

Guo, Y., D. Bozic, V. N. Malashkevich, R. A. Kammerer, T. Schulthess, and J. Engel. 1998. All-trans retinol, vitamin D and other hydrophobic compounds bind in the axial pore of the five-stranded coiled-coil domain of cartilage oligomeric matrix protein. *EMBO J.* 17:5265–5272.

Hauselmann, H. J., R. J. Fernandes, S. S. Mok, T. M. Schmid, J. A. Block, M. B. Aydelotte, K. E. Kuettner, and E. J. Thonar. 1994. Phenotypic stability of bovine articular chondrocytes after long-term culture in alginate beads. *J Cell Sci.* 107:17–27.

Hauser, N., M. Paulsson, A. A. Kale, and P. E. DiCesare. 1995. Tendon extracellular matrix contains pentameric thrombospondin-4 (TSP-4). *FEBS Lett.* 368:307–310.

Hecht, J. T., M. Deere, E. Putnam, W. Cole, B. VERTEL, H. Chen, and J. Lawler. 1998. Characterization of cartilage oligomeric matrix protein (COMP) in human normal and Pseudoachondroplasia musculoskeletal tissues. *Matrix Biol.* 17:269–278.

Hecht, J. T., L. D. Nelson, E. Crowder, Y. Wang, F. F. B. Elder, W. R. Harrison, C. A. Francomano, C. K. Prange, G. G. Lennon, M. Deere, and J. Lawler. 1995. Mutations in exon 17B of cartilage oligomeric matrix protein (COMP) cause pseudoachondroplasia. *Nat. Genet.* 10:325–329.

Hedbom, E., P. Antonsson, A. Hjerpe, D. Aeschlimann, M. Paulsson, Y. Sommarin, M. Wendel, A. Oldberg, and D. Heinegard. 1992. Cartilage matrix proteins. An acidic oligomeric protein (COMP) detected only in cartilage. *J. Biol. Chem.* 267:6132–6136.

Koh, J. L., S. J. Haas, R. Buly, and R. F. Warren. 1998. Early experience with autologous chondrocyte implantaion. *2nd Symposium of International Cartilage Repair Society* (Abstr.)

Kuhne, S. A., M. Neidhart, M. P. Everson, H. Hantzschel, P. R. Fine, S. Gay, H. J. Hauselmann, and R. E. Gay. 1998. Persistent high serum levels of cartilage oligomeric matrix protein in a subgroup of patients with traumatic knee injury. *Rheumatol. Int.* 18:21–25.

Lawler, J., F. C. Chao, and C. M. Cohen. 1982. Evidence for calcium-sensitive structure in platelet thrombospondin: Isolation and partial characterization of thrombospondin in the presence of calcium. *J. Biol. Chem.* 257:12257–12265.

Lawler, J. and R. O. Hynes. 1986. The structure of human thrombospondin, an adhesive glycoprotein with multiple calcium-binding sites and homologies with several different proteins. *J. Cell Biol.* 103:1635–1648.

Lawler, J., K. McHenry, M. Duquette, and L. Derick. 1995. Characterization of human thrombospondin-4. *J. Biol. Chem.* 270:2809–2814.

Lawler, J. and E. R. Simons. 1983. Cooperative binding of calcium to thrombospondin. The effect of calcium on the circular dichroism and limited tryptic digestion of thrombospondin. *J. Biol. Chem.* 258:12098–12101.

Misenheimer, T. M. and D. F. Mosher. 1995. Calcium ion binding to thrombospondin 1. *J. Biol. Chem.* 270:1729–1733.

Mörgelin, M., D. Heinegård, J. Engel, and M. Paulsson. 1992. Electron microscopy of native cartilage oligomeric matrix protein purified from the swarm rat chondrosarcoma reveals a five-armed structure. *J. Biol. Chem.* 267:6137–6141.

Nehrer, S., H. A. Breinan, A. Ramappa, S. Shortkroff, G. Young, T. Minas, C. B. Sledge, I. V. Yannas, and M. Spector. 1997. Canine chondrocytes seeded in type I and type II collagen implants investigated in vitro [published erratum appears in J Biomed Mater Res 1997 Winter;38(4):288]. *Journal of Biomedical Materials Research* 38:95–104.

Neidhart, M., N. Hauser, M. Paulsson, P. E. DiCesare, B. A. Michel, and H. J. Hauselmann. 1997. Small fragments of cartilage oligomeric matrix protein in synovial fluid and serum as markers for cartilage degradation. *Br. J. Rheumatol.* 36:1151–1160.

Newman, A. P. 1998. Articular cartilage repair. *Am. J. Sports. Med.* 26:309–324.

Newton, G., S. Weremowicz, C. C. Morton, N. G. Copeland, D. J. Gilbert, N. A. Jenkins, and J. Lawler. 1994. Characterization of human and mouse cartilage oligomeric matrix protein. *Genomics* 24:435–439.

Oldberg, A., P. Antonsson, K. Lindblom, and D. Heinegard. 1992. COMP (cartilage oligomeric matrix protein) is structurally related to thrombospondin. *J. Biol. Chem.* 267:22346–22350.

Petersson, I. F., T. Boegard, J. Dahlstrom, B. Svensson, D. Heinegard, and T. Saxne. 1998a. Bone scan and serum markers of bone and cartilage in patients with knee pain and osteoarthritis. *Osteoarthritis Cartilage* 6:33–39.

Petersson, I. F., T. Boegard, B. Svensson, D. Heinegard, and T. Saxne. 1998b. Changes in cartilage and bone metabolism identified by serum markers in early osteoarthritis of the knee joint. *Br. J. Rheumatol.* 37:46–50.

Qabar, A., L. Derick, J. Lawler, and V. Dixit. 1995. Thrombospondin 3 is a pentameric molecule held together by interchain disulfide linkage involving two cysteine residues. *J. Biol. Chem.* 270:12725–12729.

Robbins, J. R. and M. B. Goldring. 1998. Methods for preparation of immortalized human chondrocyte cell lines. In Methods in Molecular Medicine: Methods in Tissue Engineering. J. R. Morgan and M. L. Yarmush, editors. Humana Press, Inc, Totowa, N.J.

Rosenberg, K., H. Olsson, M. Morgelin, and D. Heinegard. 1998. Cartilage oligomeric matrix protein shows high affinity zinc-dependent interaction with triple helical collagen. *J. Biol. Chem.* 273:20397–20403.

San Antonio, J. D., J. Slover, J. Lawler, M. J. Karnovsky, and A. D. Lander. 1993. Specificity in the interactions of extracellular matrix proteins with subpopulations of the glycosaminoglycan heparin. *Biochemistry* 32:4746–4755.

Saxne, T., A. Glennas, T. K. Kvien, K. Melby, and D. Heinegard. 1993. Release of cartilage macromolecules into the synovial fluid in patients with acute and prolonged phases of reactive arthritis. *Arthritis Rheum.* 36:20–25.

Shimizu, M., K. Minakuchi, S. Kaji, and J. koga. 1997. Chondrocyte migration to fibronectin, type I collagen, and type II collagen. Cell Structure & Function. 22:309–315.

Schwartz, Z., R. M. Gilley, V. L. Sylvia, D. D. Dean, and B. D. Boyan. 1998a. The effect of prostaglandin E2 on costochondral chondrocyte differentiation is mediated by cyclic adenosine 3',5'-monophosphate and protein kinase C. *Endocrinology* 139:1825–1834.

Schwartz, Z., V. L. Sylvia, D. D. Dean, and B. D. Boyan. 1998b. The synergistic effects of vitamin D metabolites and transforming growth factor-beta on costochondral chondrocytes are mediated by increases in protein kinase C activity involving two separate pathways. *Endocrinology* 139:534–545.

Silver, F. H. and A. I. Glasgold. 1995. Cartilage wound healing. An overview. *Otolaryngol. Clin. North Am.* 28:847–864.

Sommarin, Y., T. Larsson, and D. Heinegard. 1989. Chondrocyte-matrix interactions. Attachment to proteins isolated from cartilage. *Exp. Cell Res.* 184:181–192.

Sun, X., K. Skorstengaard, and D. F. Mosher. 1992. Disulfides modulate RGD-inhibitable cell adhesive activity of thrombospondin. *J. Cell Biol.* 118:693–701. von der Mark, K., V. Gauss, H. von der Mark, and P. Muller. 1977. Relationship between cell shape and type of collagen synthesised as chondrocytes lose their cartilage phenotype in culture. *Nature* 267:531–532.

Wollheim, F. A., K. B. Eberhardt, U. Johnson, and T. Saxne. 1997. HLA DRB1* typing and cartilage oligomeric matrix protein (COMP) as predictors of joint destruction in recent-onset rheumatoid arthritis. *Br. J. Rheumatol.* 36:847–849.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An enzyme-linked immunosorbent assay kit comprising human cartilage oligomeric matrix protein prepared by the method comprising:
   a) introducing DNA encoding human cartilage oligomeric matrix protein into cells, thereby producing cells expressing human cartilage oligomeric matrix protein;
   b) culturing the cells in a culture medium under conditions suitable for expressing the human cartilage oligomeric matrix protein, thereby producing expressed human cartilage oligomeric matrix protein; and
   c) purifying the human cartilage oligomeric matrix protein in the presence of calcium.

2. An enzyme-linked immunosorbent assay kit comprising the human cartilage oligomeric matrix protein (hCOMP) produced by the method comprising:
   a) obtaining DNA encoding full length hCOMP;
   b) introducing the DNA into cells, thereby producing cells expressing hCOMP;
   c) culturing the cells in a culture medium under conditions suitable for expressing the hCOMP, thereby producing expressed hCOMP; and
   d) purifying the hCOMP in the presence of calcium.

3. A composition comprising purified cartilage oligomeric matrix protein and a biological matrix, wherein the matrix comprises at least one material selected from the group consisting of: treated cartilage and bone matrices, collagens, hyaluronan, fibrin gels, carbon fibers, porous polylactic acid, type I collagen gel, and type II collagen gel, and further comprising chondrocytes or mesenchymal stem cells.

4. A composition comprising purified cartilage oligomeric matrix protein and a biological matrix, wherein the matrix comprises at least one material selected from the group consisting of: treated cartilage and bone matrices, collagens, hyaluronan, fibrin gels, carbon fibers, porous polylactic acid, type I collagen gel, and type II collagen gel, wherein the cartilage oligomeric matrix protein is bound to a differentiation agent.

5. A composition comprising purified cartilage oligomeric matrix protein and a biological matrix, wherein the matrix comprises at least one material selected from the group consisting of: treated cartilage and bone matrices, collagens, hyaluronan, fibrin gels, carbon fibers, porous polylactic acid, type I collagen gel, and type II collagen gel and further comprising chondroitin sulfate proteoglycans.

6. A composition comprising purified cartilage oligomeric matrix protein and a biological matrix, wherein the matrix comprises at least one material selected from the group consisting of: treated cartilage and bone matrices, collagens, hyaluronan, fibrin gels, carbon fibers, porous polylactic acid, type I collagen gel, and type II collagen gel, wherein the cartilage oligomeric matrix protein is human cartilage oligomeric matrix protein purified in a calcium-replete environment.

7. A composition comprising purified cartilage oligomeric matrix protein and a biological matrix, wherein the biological matrix comprises type I collagen gel or type II collagen gel, and wherein the matrix further comprises at least one material selected from the group consisting of: treated cartilage and bone matrices, collagens, hyaluronan, fibrin gels, carbon fibers and porous polylactic acid.

8. A composition comprising purified cartilage oligomeric matrix protein and a biological matrix, wherein the matrix comprises at least one material selected from the group consisting of: treated cartilage and bone matrices, hyaluronan, fibrin gels, carbon fibers, porous polylactic acid and type I collagen gel.

\* \* \* \* \*